(12) United States Patent
Ledbetter et al.

(10) Patent No.: US 6,482,919 B2
(45) Date of Patent: Nov. 19, 2002

(54) EXPRESSION VECTORS ENCODING BISPECIFIC FUSION PROTEINS AND METHODS OF PRODUCING BIOLOGICALLY ACTIVE BISPECIFIC FUSION PROTEINS IN A MAMMALIAN CELL

(75) Inventors: Jeffrey A. Ledbetter, Seattle, WA (US); Martha S. Hayden, Everett, WA (US); Peter S. Linsley, Seattle, WA (US); Jurgen Bajorath, Everett, WA (US); H. Perry Fell, Redmond, WA (US); Lisa K. Gilliland, Oxford (GB)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/813,659

(22) Filed: Mar. 21, 2001

(65) Prior Publication Data

US 2002/0012989 A1 Jan. 31, 2002

Related U.S. Application Data

(60) Division of application No. 09/549,067, filed on Apr. 13, 2000, which is a continuation of application No. 08/539,436, filed on Oct. 5, 1995, now Pat. No. 6,132,992, which is a division of application No. 08/121,054, filed on Sep. 13, 1993, now Pat. No. 5,637,481, which is a continuation-in-part of application No. 08/013,420, filed on Feb. 1, 1993, now abandoned.

(51) Int. Cl.$^7$ ..................... C07K 16/28; C07K 14/705; C07K 16/46
(52) U.S. Cl. .................... 530/324; 530/350; 530/387.1; 530/387.3; 530/387.9; 530/327; 530/328; 530/329; 530/330
(58) Field of Search .............................. 435/320.1, 455, 435/456, 69.1; 530/350, 324, 387.1, 387.3, 387.9, 327, 328, 329, 330

(56) References Cited

U.S. PATENT DOCUMENTS 5,637,481 A 6/1997 Ledbetter et al.
6,132,992 A * 10/2000 Ledbetter et al. .......... 435/69.7

OTHER PUBLICATIONS

Anderson et al., "Crosslinking of T3 (CD3) With T4 (CD4) Enhances The Proliferation of Resting T Lymphocytes" *J. Immunol.*, 1987, 139:678–682. (Exhibit 1).

Capon et al., "Designing CD4 Immunoadhesions for AIDS Therapy", *Nature*, 1989, 337:525–531. (Exhibit 2).

Chappel et al., "Identification of the Fc Receptor Class I Binding Site in Human IgG Through the Use of Recombination IgG/IgG2 Hybrid and Point–Mutated Antibodies" *Proc. Natl. Acad. Sci. USA*, 1991, 88:9036–9040. (Exhibit 3).

Davis et al., "Single Chain Antibody (SCA) encoding Genes: One Step Construction and Expression In Eukaryotic Cells" *Biotechnology*, 9:165–169. (Exhibit 4).

Emmerich et al., "Selective Stimulation of Human T Lymphocyte Subsets by Heteroconjugates of Antibodies to the T–cell Receptor and to Subset–specific Differentiation Antigens" *Eur. J. Immunol*, 1988, 18:645–648. (Exhibit 5).

Ford et al., "Fusion Tails for the Recovery and Purification of Recombinant Proteins" *Protein Expression and Purification*, 1991, 2:95–107. (Exhibit 6).

Fouser et al., "High Level Expression of a Chimerc Antigen–Ganglioside GD2 Antibody: Genomic Kappa Sequences Improve Expression in COS and CHO Cells", *Biotechnology*, 1992, 10:1121–1127, (Exhibit 7).

Hieter et al., "Cloned Human and Mouse Kappa Immunoglobulin Constant and J Region Genes Conserve Homology in Functional Segments", *Cell*, 1980, 22:197–207. (Exhibit 8).

Jung et al., "Induction of Cytotoxicity in Resting Human T Lymphocytes bound to Tumore Cells by Antibody Heteroconjugates", *Proc. Natl. Acad. Sci. USA*, 1987, 84:4611–4615. (Exhibit 9).

Ledbetter et al., "Signal Transduction Through CD4 Proximity to the CD3/T Cell Receptor", *Eur. J. Immunol.*, 1988, 18:525–532. (Exhibit 10).

Ledbetter et al., "Enhanced Transmemebrane Signalling Activity of Monoclonal Antibody Heterconjugates Suggest Molecular Interactions Between Receptor on the T Cell Surface", *Mol. Immunol.*, 1989, 26:137–145. (Exhibit 11).

Linsley et al., "Binding of the B Cell Activation Antigen B7 to CD28 Costimultes T Cell Proliferation and Interleukin 2 mRNA Accumulation", *J. Exp. Med.*, 1991, 173:721–730. (Exhibit 12).

Liu et al., "Heteroantibody Duplexes Target Cells for Lysis by cytotoxic T Lymphocytes", *Proc. Natl. Acad. Sci. USA*, 1985, 82:8648–8652. (Exhibit 13).

Liu et al., "Chimeric Mouse–Human IgG1 Antibody that can Mediate Lysis for Cancer Cells", *Proc. Natl. Acad. Sci. USA.*, 1987, 84:3439–3443. (Exhibit 14).

Lund et al., "Human Fc RI and Fc RII Interact with Distinct but Overlapping Sites on Human IgG", *Journal of Immunology*, 1991, 147:2657–2662. (Exhibit 15).

Mayforth et al., "Current Concepts: Designer and Catalytic Antibodies", *New Eng. J. Med.*, 1990, 323:173–178. (Exhibit 16).

Morrison et al., "In Vitro Antibodies: Strategies for Production and Application", *Ann. Rev. Immunol.*, 1992, 10:239–266. (Exhibit 17).

(List continued on next page.)

*Primary Examiner*—David Guzo
(74) *Attorney, Agent, or Firm*—Audrey F. Sher

(57) ABSTRACT

The present invention provides novel soluble CTLA4Ig molecules having modified Ig domains.

6 Claims, 18 Drawing Sheets

OTHER PUBLICATIONS

Neuberger et al., "Recombinant Antibodies Possesing novel Effector Functions", *Nature,* 1984, 312:604–608. (Exhibit 18).

Orlandi et al. "Cloning Immunoglobulin Variable Domains for Expression by the Polymerase Chain Reaction", *Proc. Nat. Acad. Sci. USA,* 1989, 86:3833–3837. (Exhibit 19).

Perez et al., "Specific Targeting of Cytotoxic T Cells by Anti–T3 Linked to Anti–Target Cell Antibody", *Nature,* 1985, 316:354–356. (Exhibit 20).

Perez et al., "Specific Targeting of Cytotoxic T Cells by Anti–T3 Linked to Anti–Target Cell Antibody", *Nature,* 1985, 316:354–356. (Exhibit 20).

Shopes, B. "A Genetically Engineered Human IgG Mutant Cytolytic Activity", *Journal of Immunology,* 1992, 148(9):2918–2922. (Exhibit 22).

Staerz et al., "Hybrid Hybridoma Producing a Bispecific Monoclonal Antibody that can Focus Effector T–Cell Activity", *Proc. Natl. Acad. Sci. USA,* 1986, 83:1453–1457. (Exhibit 23).

Traunecker et al., "Bispecific Single Chain Molecules(Janusins) Target Cytotoxi Lymphocytes on HIV Infected Cells", *EMBO,* 1991, 10:3655–3659. (Exhibit 24).

Emmrich et al., "Synergism in the Activation of Human CD8 T Cells by Cross–Linking the T–Cell Receptor Complex with the CD8 Differentation Antigen", *Proc. Natl. Acad. Sci. USA,* 1986, 83:8298–8302. (Exhibit 25).

Wels et al., "Construction, Bacterial Expression and Characterization of a Bifunctional Single–Chain Antibody Phosphatase Fusion Protein Targeted to the Human ERBB–2 Receptor", *Biotechnology,* 1992, 10:1128–1132. (Exhibit 26).

Winter et al., "Man Made Antibodies", *Nature,* 1991, 349:293–299. (Exhibit 27).

Pluckthun, A. "Mono–and Bivalent Antibody Fragments Produced in *Escherichia coli:* Engineering, Folding and Antigen Binding", *Immunological Reviews,* 1992, 103:151–188. (Exhibit 28).

Emmrich et al., "Synergism in the Activation of Human CD8 T Cells By Cross–linking the T–Cell Receptor complex with the CD8 Differentiation Antigen", *Proc. Natl. Acad. Sci. USA,* 1986, 83:8298–8302. (Exhibit 29) Bird et al., "Single–Chain Antigen–Binding Proteins", *Science,* 1988, 24:423–426. (Exhibit 30).

Hollinger et al., "Diabodies: Small bivalent and Bispecific Antibody Fragments", *Proc. Natl. Acad. Sci. USA,* 1993, 90:6444–6448. (Exhibit 31).

Adams, GP et al., "Highly specific in vivo tumor targeting by monovalent and divalent forms of 741F8 anti–c–erbB–2 single–chain Fv.", *Cancer Res.,* 1993, Sep. 1; 53(17):4026–34. (Exhibit 32).

Huston, JS et al., "Antigen recognition and targeted delivery by the single–chain F," *Cell Biophys,* 1993, Jan.–Jun.; 22(1–3): 189–224. (Exhibit 33).

Huston, JS. "Multisite association by recombinant proteins can enhance binding selectivity. Preferential removal of immune complexes from serum by immobilized truncated FB analogues of the B domain from staphylococcal protein A", *Biophys J.,* 1992, Apr.; 62(1):87–91, (Exhibit 34).

McCarteny, JE et al., "Biosynthetic antibody binding sites; development of a sing–chain Fv model based on antidinitrophenol IgA myeloma MOPC 315", *J. Protein Chem.,* 1991, Dec.; 10(6):669–83. (Exhibit 35).

Tai, MS et al., "A bifunctional fusion protein containing Fc–binding fragment B of staphylococcal protein A amino terminal to antidigoxin Single–chain Fv," *Biochemistry,* 1990, Sep. 4;29(35):8024–30. (Exhibit 36).

Huston, JS et al., "Protein engineering of single–chain Fv analogs and fusion proteins", *Methods Enzymol,* 1991, 203:47–89. (Exhibit 37).

Whitlow, M. and D. Filpula, "Single–chain Fv Proteins and Their Fusion Proteins," *Methods: A Companion ot Methods in Enzymology,* 1991, 2:97–105. (Exhibit 38).

Whitlow, M. et al., "An Improved Linker for Single Chain Fv with Reduces Aggregation and Enhanced Proteolytic Stability," *Protein Eng.,* 1993, 6:989–95. (Exhibit 39).

Batra, J. K. et al., "Anti–TAC (Fv) PE40, A Single Chain Antibody Pseudomans Fusion Protein Directed at Interleukin 2 Receptor Bearing Cells," *J. Biol. Chem.,* 1990, 265:15198–202. (Exhibits 40).

Brinkmann, U. et al., "B3 (Fv)–PE38KDEL, a Single–Chain Immunotoxin That Causes Complete Regression of a Human Carcinoma in Mice," *Proc. Natl. Acad. Sci USA,* 1991, 88:8616–20. (Exhibit 41).

Goshorn, S. C. et al., "Genetic Construction, Expression and Characterization of a Single–Chain Anti–Carcinoma Fused to β–lactamase.," *Cancer Res.,* 1993, 53:2123–7. (Exhibit 42).

Fell, H.P. et al., "Genetic Construction and Characterization of a Fusion Protein Consisting of a Chimeric F(ab') with Specificity for Carcinomas and Human IL–2," *J. Immunol.,* 1991, 146:2446–52. (Exhibit 43).

Gillies, S. D. et al., "Antibody Targeted Interleukin 2 Stimulates T Cell Killing of Autologous Tumor Cells," *Proc. Natl. Acad. Sci USA,* 1992, 89:1428–32. (Exhibit 44).

Blondel et al., *Protein Engineeering,* 1991, 4(4):457–61. (Exhibit 45).

Pack et al., *Biochem.,* 1992, 31(6):1579–84. (Exhibit 46).

Balzano et al., *Int. J. Cancer Suppl.,* 1992, 7:28–32. (Exhibit 47).

Gimmi et al., *PNAS USA,* 1991, 88:6575–79. (Exhibit 48).

Harper et al, *J. Immunol.,* 1991, 147(3):1037–44. (Exhibit 49).

Kubota et al., *J. Immunol.,* 1990, 145(11):3924–3931. (Exhibit 50).

Marken et al., *PNAS USA,* 1992, 89:3503–7. (Exhibit 51).

* cited by examiner

| Fc CONSTRUCT | SEQUENCE | | ADCC | CDC |
|---|---|---|---|---|
| | HINGE | CH2 | | |
| CHIMERIC L6 | DQEPKSCDKTHTCPPCP | APELLGGPSVFLP | YES | YES |
| WTD | DQEPKSCDKTHTCPPCP | APELLGGPSVFLP | YES | NO |
| DM1 | DQEPKSCDKTHTCPPCP | APEFEGAPSVFLP | NO | NO |
| HS1 | DQEPKSSDKTHTSPPSP | APELLGGPSVFLP | YES | NO |
| HS2 | DQEPKSSDKTHTSPPSP | APELLGGSSVFLP | NO | NO |
| HS3 | DQEPKSSDKTHTSPPSP | APEFEGAPSVFLP | NO | NO |

EXPRESSION VECTORS ENCODING BISPECIFIC FUSION PROTEINS AND METHODS OF PRODUCING BIOLOGICALLY ACTIVE BISPECIFIC FUSION PROTEINS IN A MAMMALIAN CELL

This application is a divisional application of U.S. Ser. No. 09/549,067, filed Apr. 13, 2000, which is a continuation application of U.S. Ser. No. 08/539,436 filed Oct. 5, 1995, now U.S. Pat. No. 6,132,992, which is a divisional application of U.S. Ser. No. 08/121,054 filed Sep. 13, 1993, now U.S. Pat. No. 5,637,481, which is a continuation-in-part application of U.S. Ser. No. 08/013,420, filed Feb. 1, 1993, now abandoned, the contents of all of which are incorporated by reference into the present application.

Throughout this application various publications are referenced. The disclosures of these publications in their entireties are hereby incorporated by reference into this application in order to more fully describe the state of the art to which this invention pertains.

The present invention relates to expression vectors encoding bispecific fusion proteins and methods for producing a biologically active bispecific fusion protein in a mammalian cell.

BACKGROUND OF THE INVENTION

Because of the problems associated with traditional antibody technology such as obtaining antibody from sera or hybridoma technology, genetic engineering has been used with increasing frequency to design, manipulate, and produce antibodies or antibody derivative molecules (such as bispecific fusion proteins) with a desired set of binding properties and effector functions.

Difficulties encountered with the production of stable hybridomas producing human antibody have led to the development of alternative technologies designed to circumvent in vivo antibody production and conventional in vitro techniques (Mayforth R. D., Quintans, J. (1990) Current Concepts: Designer and catalytic antibodies. New Eng. J. Med. 323:173–178; Waldmann, T. A. (1991) Monoclonal antibodies in diagnosis and therapy. Science 252:1657–1662; Winter, G., Milstein, C. (1991) Man-made Antibodies. Nature 349:293–299; Morrison, S. L. (1992) In Vitro antibodies: strategies for production and application. Ann. Rev. Immunol. 10:239–266).

Initial attempts to couple the binding specificities of two whole antibodies against different target antigens for therapeutic purposes utilized chemically conjugated "heteroconjugate" molecules (Staerz, U. D., Kanagawa, O., Becan, M. J. (1985) Hybrid antibodies can target sites for attack by T cells. Nature 314:628–631; Perez, P., Hoffman, R. W., Shaw, S., Bluestone, J. A., Segal, D. M. (1985) Specific targeting of cytotoxic T cells by anti-T3 linked to anti-target antibody. Nature 316:354–356; Liu, M. A., Kranz, D. M., Kurnick, J. T., Boyle, L. A., Levy, R., Eisen, H. N. (1985) Heteroantibody duplexes target cells for lysis by cytotoxic T lymphocytes. Proc. Natl. Acad. Sci. USA 82:8648–8652; Jung, G., Ledbetter, J. A., Muller-Eberhard, H. J. (1987) Induction of cytotoxicity in resting human T lymphocytes bound to tumor cells by antibody heteroconjugates. Proc. Natl. Acad. Sci. USA 84:4611–4615; Emmrich, F., Rieber, P., Kurrie, R., Eichmann, K. (1988) Selective stimulation of human T lymphocyte subsets by heteroconjugates of antibodies to the T cell receptor and to subset-specific differentiation antigens. Eur. J. Immunol. 18:645–648; Ledbetter, J. A., June, C. H., Rabinovitch, P. S., Grossmann, A., Tsu, T. T., Imboden, J. B. (1988) Signal transduction through CD4 proximity to the CD3/T cell receptor. Eur. J. Immunol. 18:525–532).

These attempts demonstrated that monoclonal antibodies directed against the murine or human CD3 T cell surface receptor chemically linked to anti-target cell antibodies trigger lysis of target cells by cytotoxic T lymphocytes (CTL), overcoming the major histocompatibility complex restriction of CTL.

Bispecific antibodies have been produced from hybrid hybridomas by heterohybridoma techniques and have demonstrated properties in vitro similar to those observed for heteroconjugates (Milstein, C., Cuello, A. C. (1983) Hybrid hybridomas and their use in immunohistochemistry. Nature 305:537–540; Staerz, U. D., Bevan, M. J. (1986) Hybrid hybridoma producing a bispecific monoclonal antibody that can focus effector cell activity. Proc. Natl. Acad. Sci. USA 83:1453–1457; Clark, M. R., Waldmann, H. (1987) T-cell killing of target cells induced by hybrid antibodies: comparison of two bispecific monoclonal antibodies. J. Natl. Cancer Inst. 79:1393–1401; Lanzavecchia, A., Scheidegger, D. (1987) The use of hybrid hybridomas to target cytotoxic T lymphocytes. Eur. J. Immunol. 17:105–111; Gilliland, L. K., Clark, M. R., Waldmann, H. (1988) Universal bispecific antibody for targeting tumor cells for destruction by cytotoxic T cells. Proc. Natl. Acad. Sci. USA 85:7719–7723). However, such antibodies were produced from cell fusions.

Despite the promising results obtained using heteroconjugates or bispecific antibodies from cell fusions, several factors made them impractical for large scale therapeutic applications. Such factors include (1) rapid clearance of large heteroconjugates in vivo, (2) the labor intensive techniques required for generating either type of molecule, (3) the need for extensive purification away from the homoconjugates or mono-specific antibodies, and (4) low yields.

Generally, procedures associated with using heteroconjugates or bispecific antibodies involve co-expression approaches with two different specificities in which the sequences encoding the heavy (H) and/or light (L) immunoglobulin chains are not linked and thus suffer from the problem of random H-L association, and/or random (HL)-(HL) association, leading to only a small percentage of correct product and to difficult purification schemes. Purification may become cumbersome and the characterization difficult, if there is an excessive number of monospecific or non-specific protein molecules.

In an effort to eliminate these problems, genetic engineering has been used to generate bispecific or bifunctional single chain antibodies in vitro (Haber et al., 1990; Wels, W., Harwerth, I. M., Zwickl, M., Hardman, N., Groner B., Hynes, N. E. (1992) Construction, bacterial expression and characterization of a bifunctional single-chain antibody phosphatase fusion protein targeted to the human ERBB-2 receptor. Biotechnology 10:1128–1132; A. Traunecker et al. (1991) EMBO Journal 10(12):3655–3659). However, such efforts have not been promising.

Bispecific or bifunctional single chain antibodies have been produced in a bacterial system. However, such fusion proteins have been produced in inactive form (Haber et al., 1990). Further, the fusion proteins so produced exhibit reductions in binding affinities and/or avidities or require complicated isolation and purification procedures to recover the desired products (Haber et al., 1990; Wels et al., 1992a).

Monovalent single chain antibodies and bifunctional single chain antibodies have been expressed (Wels, 1992b). The antibody molecules were genetically engineered to minimize their size and to allow for their functional modification. Moreover, the bifunctional antibody is bifunctional only in that the bacterial alkaline phosphatase gene was joined 3' to the $scF_v$ gene. These bifunctional antibodies include a single binding domain (e.g., $V_L+V_H$) and the alkaline phosphatase gene was used merely as a marker to detect the antibodies so bound to its target.

Janusin molecules containing FvCD3 and CD4 sequences have been expressed (A. Traunecker et al. "Bispecific single chain molecules (Janusins) target cytotoxic lymphocytes on HIV infected cells, EMBO Journal 10(12):3655–3659). The janusin construct comprises a portion of the CD4 molecule in the amino terminus of the construct and the binding domain (i.e., $V_L+V_H$) of CD3 in the carboxy terminus of the construct. Janusin molecules do not comprise helical peptide linkers which separate the CD3 variable regions from portions of the CD4 molecule. Moreover, janusin molecules are sometimes found in multimeric or aggregate forms. Additional purification is sometimes required to avoid aggregate formation.

There is a need for the subject invention in view of the problems discussed hereinabove concerning antibody production. At present, there is a persisting problem associated with antibody technology, namely, the difficulty in obtaining large quantities of specific antibody. Historically, antibodies were obtained from sera or hybridomas of mouse origin. However, sera were often of limited quantity and variable quality. Moreover, antibodies of mouse origin have limited usefulness for human treatment because of their propensity to initiate an immune response sometimes deleterious to non-mouse subjects.

In order to overcome the problems which specifically plague antibody technology and more generally the problems associated with the production of substantial amounts of functional protein molecules, a new expression vector which facilitates the expression of biologically active fusion proteins is described herein.

SUMMARY OF THE INVENTION

The present invention provides an expression vector encoding monospecific or bispecific fusion protein.

In one embodiment, the expression vector encodes a monospecific fusion protein (e.g., FIG. 9), which vector comprises a recombinant monospecific single chain cassette comprising a DNA sequence encoding a first binding domain capable of binding a target such as a cell surface antigen.

In another embodiment, the expression vector encodes a bispecific fusion protein; the vector comprises a recombinant bispecific single chain cassette comprising a DNA sequence encoding a first binding domain capable of binding a target and a DNA sequence encoding a second binding domain capable of binding a target, each domain capable of binding a different target.

The present invention also provides a method for producing a biologically active monospecific or bispecific fusion protein in a mammalian cell. This method comprises: (a) transfecting the mammalian cell with the recombinant expression vector of the invention; (b) culturing the mammalian cell so transfected in step (a); and (c) recovering the biologically active bispecific fusion protein so produced by the cultured mammalian cell.

DETAILED DESCRIPTION OF THE INVENTION

Definitions

Figure 1:
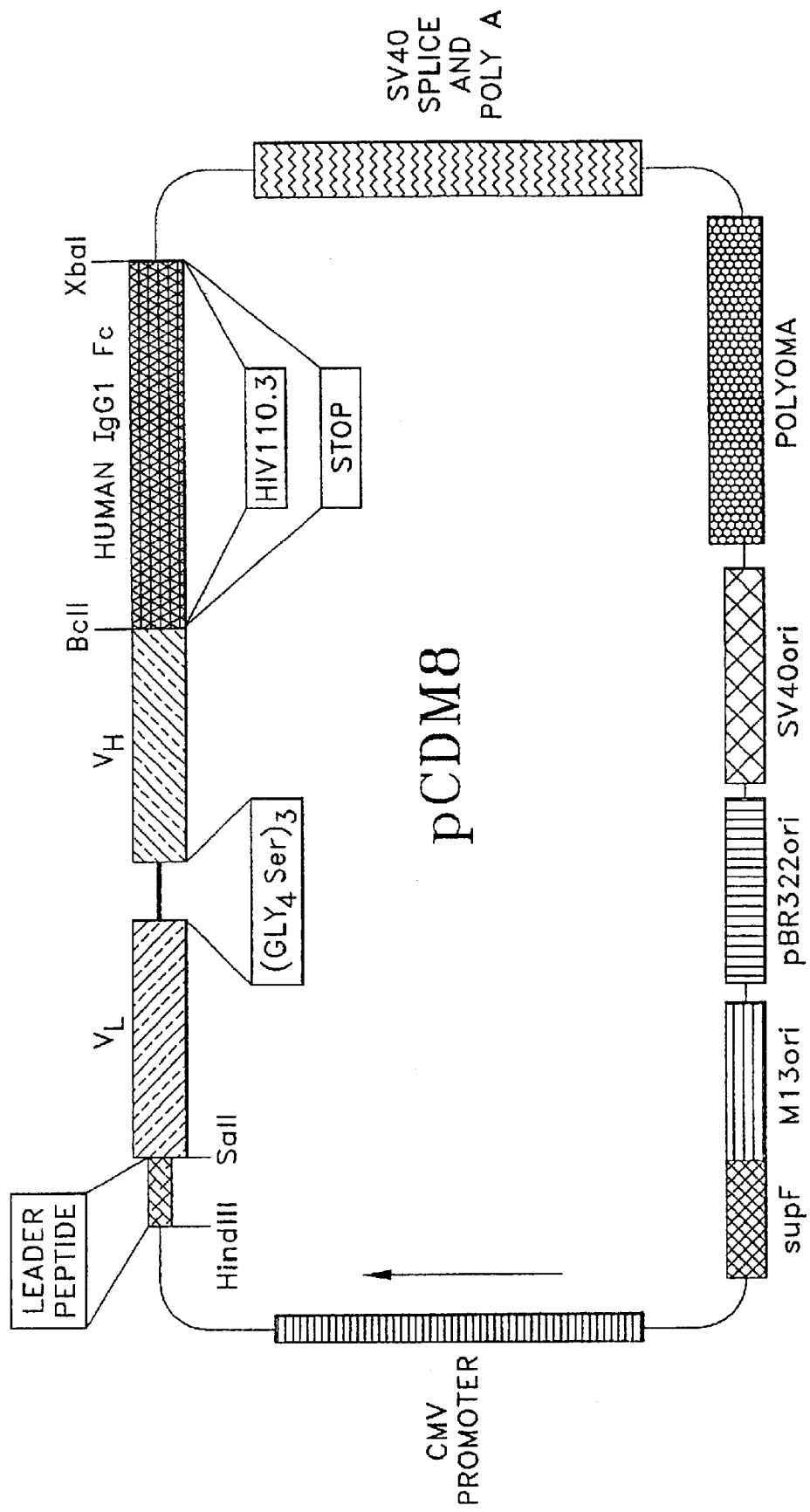
FIG. 1 is a diagram of the pCDM8 expression vector including the recombinant monospecific single chain cassette including different molecular tags, or a simple stop codon.

As used in this application, the following words or phrases have the meanings specified.

As used herein, a "bispecific fusion protein" means any immunologically reactive molecule which specifically recognizes and binds at least two different targets at alternate times or at the same time and is expressed as a single chain.

As used herein, a "monospecific fusion protein" means any immunologically reactive molecule which specifically recognizes and binds a target and is a complex comprising two heavy immunoglobulin chains, two light immunoglobulin chains, or a heavy and/or light immunoglobulin chain and/or any portions thereof and is expressed as a single chain.

As used herein, an "expression vector" means a nucleic acid molecule comprising (1) a promoter and other sequences (e.g. leader sequences) necessary to direct expression of a desired gene or DNA sequence and (2) the desired gene or DNA sequence. Optionally, the nucleic acid molecule may comprise a poly A signal sequence to enhance the stability of the gene transcript and/or an enhancer sequence to increase the transcription of the gene thereby affecting the expression of the gene.

As used herein, a "binding domain" means a binding site which recognizes and binds the entire binding area of a target or any portion thereof. Examples include, but are not limited to, (1) a single variable region of an antibody (V$_L$ or V$_H$); (2) two or more variable regions (e.g. V$_L$+V$_H$; V$_L$+V$_L$; or V$_H$+V$_H$) or the complementary determining region (CDR) thereof, or (3) an antigen (such as a leucocyte antigen) or a portion thereof.

As used herein, a "molecular tag" includes any DNA sequence encoding a molecule which may facilitate detection and purification of the fusion proteins described herein.

As used herein, a "bispecific single chain cassette" includes a DNA sequence encoding a first binding domain capable of binding a target and a DNA sequence encoding a second binding domain capable of binding a target, each domain capable of binding a different target at alternate times or at the same time, both domains encoded by DNA sequences being on the same cassette. The first and/or second binding domains may be two variable regions (V$_L$+V$_H$, V$_H$+V$_L$, V$_L$+V$_L$, or V$_H$+V$_H$) or a single variable region (V$_L$ or V$_H$). Alternatively, the first and/or second binding domains may be an antigen or portion thereof. Suitable examples of antigens include but are not limited to the leucocyte antigens. The first binding domain is located in or towards the amino terminus of the expressed protein while the second binding domain is located in or towards the carboxy terminus of the expressed protein (corresponding to the 5' or 3' end, respectively, of the DNA sequences of the bispecific single chain DNA cassette).

As used herein, a "single chain cassette" means a sequence which encodes proteins being able to recognize and bind at least a portion of its target. Such proteins may have multiple sites for recognizing and binding multiple targets.

In order that the invention herein described may be more fully understood, the following description is set forth.

A. VECTORS

The expression vector described herein may be modified by wholly or partially replacing particular DNA sequences encoding binding domains (i.e., the coding sequences thereof) or regulatory sequences, i.e. a promoter or other sequences necessary to direct expression of the desired gene (e.g., leader sequences), within the expression plasmid.

The DNA sequence so replaced in the modified expression vector may encode any variable region of any antibody or other receptor. For example, the DNA sequence may encode the variable region or regions of an antibody which recognizes and binds the BR96 antigen, CD3, L6, CD28, CTLA4, or B7. Additionally, the DNA sequence may encode variable regions capable of binding to other cell surface antigens. Alternatively, the binding domains may encode all or part of an antigen such as the leucocyte antigen. The primary consideration on whether to insert a particular replacement sequence is whether the sequence so replaced is positioned "in-frame" so that the desired binding domain can be expressed.

The sequences so replaced may be cloned by the method of polymerase chain reaction (PCR). PCR may be used to produce a multiplicity of DNA sequences which can be inserted into the expression vector which in turn can transform a eucaryotic cell and thereby express the DNA sequence. Other cloning methods, e.g., ligase chain reaction (LCR), that achieve multiplication of specific sequences can also be used.

The promoter of the expression vector may be easily replaced with other promoters depending on the type of cells used for expression or the DNA sequence being inserted. Suitable examples of promoters include cytomegalovirus (CMV), avian myeloblastosis virus (AMV) and Moloney murine leukemia virus (MMLV).

Antibodies in their native, monomeric form are four-chain macromolecules containing two identical heavy chains and two identical light chains per molecule. Each chain is made up of a variable (V) region and a constant (C) region. The variable region of the light chain ($V_L$) is encoded by variable (V) plus joining (J) region genes; the variable region of the heavy chain ($V_H$) is encoded by variable (V) plus joining (J) region genes with an intervening diversity (D) region. Each variable region fragment ($V_L$ or $V_H$) encoded by $V_L+J_L$ or by $V_H+D_H+J_H$ sequences is composed of approximately 100 amino acids. Contained within these sequences are three regions of hypervariability called complementarity determining regions (CDR) that appear to contain the amino acids that line the antibody's combining site. The CDRs are interspersed in four regions of much lower variability called framework regions (FR).

The antigen binding pocket of the antibody is typically formed by the association of $V_L$ and $V_H$ region polypeptides into their β-pleated sheet conformation, with the CDR regions contained at, or near, the loops between strands. Occasionally the $V_L+V_L$ pairs or the $V_H+V_H$ pairs (e.g. G17–2 light chain monomers) or the $V_L$ or $V_H$ alone can bind antigen.

Therefore, the "binding domain" comprises one or a combination of the following: (a) a $V_L$ plus a $V_H$ region of an immunoglobulin (IgG, IgM or other immunoglobulin), (b) a $V_L$ plus $V_L$ region of an immunoglobulin (IgG, IgM or other immunoglobulin), (c) a $V_H$ plus $V_H$ region of an immunoglobulin (IgG, IgM or other immunoglobulin), (d) a single $V_L$ region of an immunoglobulin (IgG, IgM or other immunoglobulin), or (e) a single $V_H$ region of an immunoglobulin (IgG, IgM or other immunoglobulin).

Expression vectors according to the present invention are not limited to vectors incorporating antibody sequences. Sequences encoding binding domains of other types of proteins such as antigens and receptors can also be used. Thus, the vectors encode bispecific fusion proteins which can bind different multiple targets, at alternate or at essentially the same time.

In one embodiment of the present invention, the recombinant single chain cassette comprises multiple DNA sequences encoding multiple (1) variable regions and/or (2) antigens or portions thereof, each with distinct specificities. In the cassette, the sequence encoding a variable region is preferably joined to DNA encoding a) another variable region or b) an antigen or antigens, by linkers, all of which are arranged in tandem. Typically, such linkers are helical in structure. Helical peptide linkers permit proper folding of the protein molecule. Further, helical peptide linkers may enhance the solubility of the molecule. In contrast to expressing a single variable region alone ($V_L$ or $V_H$), two variable regions as a single chain protein ($V_L+V_H$; $V_L+V_L$; $V_H+V_H$) require linking of the individual variable regions by short linkers, e.g., $(Gly_4Ser)_3$ (residues 134–148 of SEQ ID NO:18) linkers.

A whole range of short linkers may be used to join immunoglobulin chains of a $V_L+V_H$ (FV) fragment (Huston, J. S., Levinson, D., Mudgett-Hunter, M., Tai, M.S., Novotny, J., Margolies, M. N., Ridge, R. J., Bruccoleri, R. E., Haber, E., Crea, R., Oppermann, H. (1988) Protein engineering of antibody binding sites: recovery of specific activity in an antidigoxin single-chain Fv analogue produced in *Escherichia coli*. Proc. Natl. Acad. Sci. USA 85:5879–5883; Pluckthün, 1991). Such linkers are passive entities during protein folding. Generally such linkers are hydrophilic and flexible.

Conventionally, there are several means for linking the immunoglobulin chains of a $F_v$ fragment, i.e. by chemical cross-linking (Glockshuber et al., 1991); natural cross-linking by disulfide bonds (Glockshuber, 1990a); natural association without disulfide bonds; and connecting by a genetically encoded peptide linker (Bird, R. E., Hardman, K. D., Jacobson, J. W., Johnson, S., Kaufman, B. M., Lee, S. M., Lee, T., Pope, S. H., Riordan, G. S., Whitlow, M. (1988) Single-chain antigen-binding proteins. Science 242:423–427; Huston et al., 1988a).

The single chain cassettes may comprise multiple linkers. The primary limitation on the number of linkers is that number which still permits the expression of functional fusion proteins encoded by the vectors of the invention.

Linkers encoding helical peptides of the invention (e.g., SEQ ID NOS: 10, 11, 12) may be modified, i.e., by amino acid substitutions within the molecule, so as to produce derivative molecules thereof. Such derivative molecules would retain the functional property of the helical peptide linker, namely, the molecule having such substitutions will still permit the expression of the biologically active protein product encoded by the novel expression vector of the invention.

These amino acid substitutions include, but are not necessarily limited to, amino acid substitutions known in the art as "conservative".

For example, it is a well-established principle of protein chemistry that certain amino acid substitutions, entitled "conservative amino acid substitutions," can frequently be made in a protein without altering either the conformation or the function of the protein. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa.

Other substitutions can also be considered conservative, depending on the environment of the particular amino acid and its role in the three-dimensional structure of the protein. For example, glycine (G) and alanine (A) can frequently be interchangeable, as can alanine and valine (V).

Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

Vectors encoding fusion proteins comprising antibody variable regions with light and/or heavy chain sequences and non-antibody binding domain or domains are encompassed by the present invention. The first and/or the second binding domains may be a variable region or regions of an antibody. Alternatively, the first and/or the second binding domains may be an antigen or a portion or portions thereof. Preferably the portion of the antigen includes that portion that can be recognized and to which a molecule can bind after recognition. For example, in a-transmembrane protein antigen, the prefered portion would be the extracellular portion. However, other portions are also encompassed by the invention.

Examples of suitable antigens and receptors include, but are not limited to, CD and non-CD molecules.

CD molecules include, but are not limited to, CD1, CD2, CD3/TcR, CD4, CD5, CD6, CD7, CD8, CD9, CD10, CD11, CD12, CD13, CD14, CD15, CD16, CDw17, CD18, CD19, CD20, CD21, CD22, CD23, CD24, CD25, CD26, CD27, CD28, CD29, CD30, CD31, CDw32, CD33, CD34, CD35, CD36, CD37, CD38, CD39, CD40, CD41, CD42a,b, CD43, CD44, CD45, CD46, CD47, CD48, CD49, CDw50, CD51., CDw52, CD53, CD54, CD55, CD56, CD57, CD58, CD59, CDw60, CD61, CD62, CD63, CD64, CDw65, CD66, CD67, CD68, CD69, CDw70, CD71, CD72, CD73, CD74, CDw75, CD76, CDw78.

Non-CD molecules include, but are not limited to, B7, B7 (2), CTLA4, BR96, GP39, LFA-3, ICAM-2, and interleukin (IL) 1–8.

For example, CD28 antigen is a homodimeric glycoprotein of the immunoglobulin superfamily (Aruffo, A., Seed, B. (1987) Molecular cloning of a CD28 cDNA by a high-efficiency COS cell expression system. Proc. Natl. Acad. Sci. USA 84:8573–8577) found on most mature human T cells (Damle et al. (1983) J. Immunol. 131:2296–2300). Monoclonal antibodies (mAbs) reactive with CD28 antigen can augment T cell responses initiated by various polyclonal stimuli. A homologous molecule, CTLA4 has been identified by differential screening of a murine cytolytic-T cell cDNA library (Brunet et al. (1987) Nature 328:267–270).

The expression vectors of the invention encompass vectors capable of encoding multi-specific fusion proteins, i.e., a molecule capable of reacting with many targets. For example, the expression vector may encode a trispecific fusion protein capable of being expressed in a single chain, namely, a fusion protein which recognizes and binds to three targets. Alternatively, the fusion protein may recognize and bind four targets.

Figure 9:
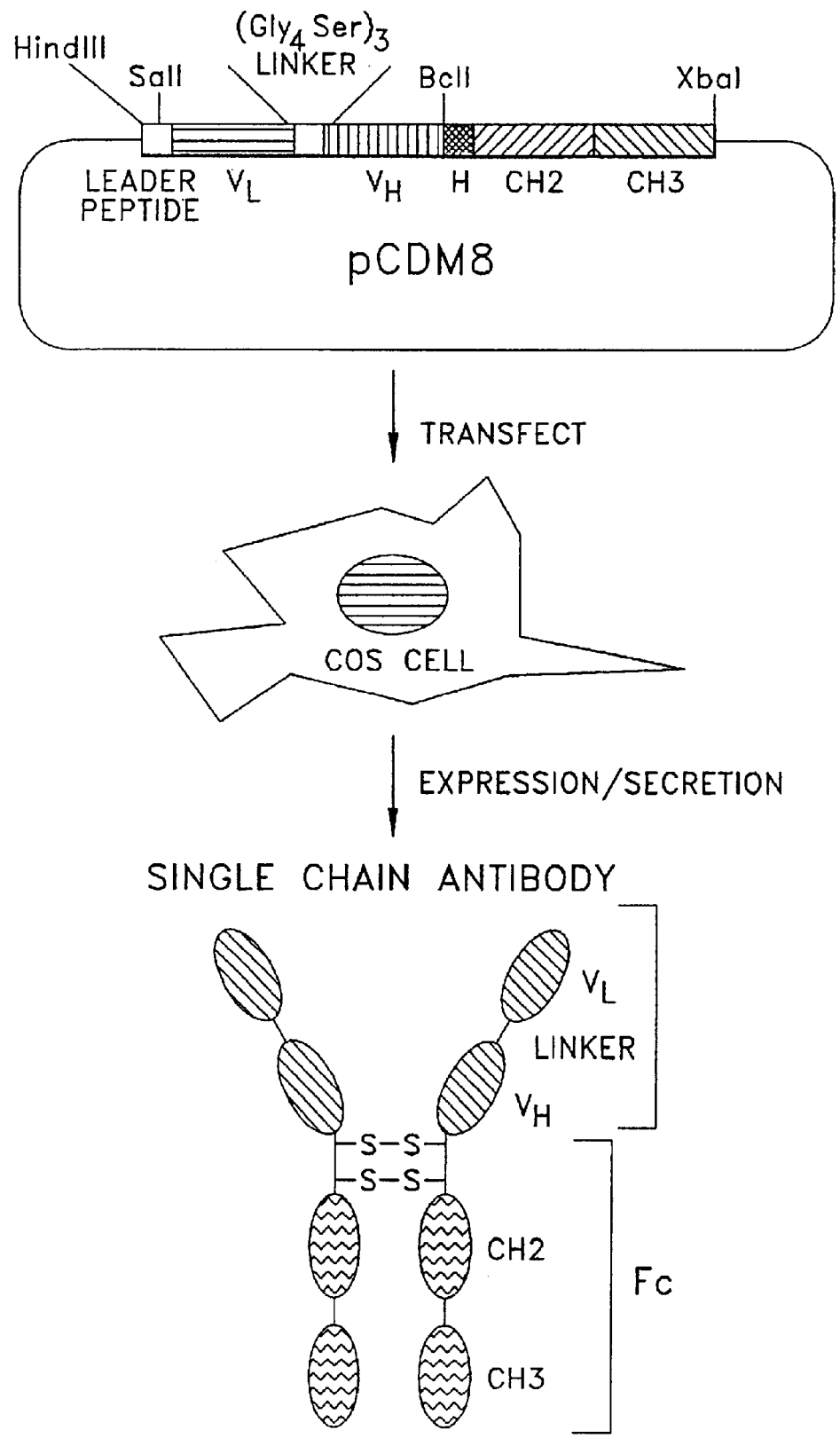
FIG. 9 is a schematic diagram showing the modification of the expression vector pCDM8 for expression of the monospecific antibody variable regions as fusion proteins with the Fc domain from human IgG1.
Figures 10A, 10B:
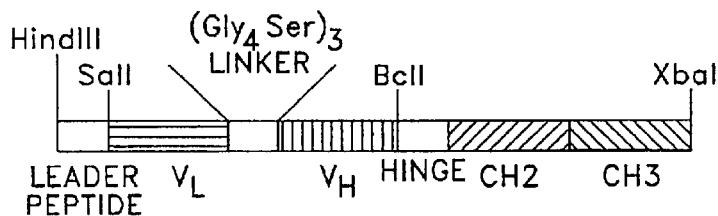
FIG. 10A is a diagram of the structure of L6FV-Ig derivatives, with linker sequences indicated by the black lines and each functional domain indicated by a shaded box.
FIG. 10B is a comparison of the Fc construct of chimeric L6 (SEQ ID NO:24), WTD (SEQ ID NO:24), DM1 (SEQ ID NO:25), HS1 (SEQ ID NO:26), HS2 (SEQ ID NO:27), and HS3 (SEQ ID NO:28) including their sequences, and whether they exhibit ADCC or CDC activity. The L6 Fv was fused to several different mutant derivatives of the Fc domain from human IgG1. The sequence changes introduced into the hinge and/or the CH2 domain are indicated by underlined amino acids, with the construct identification listed to the left.
Figure 10C:
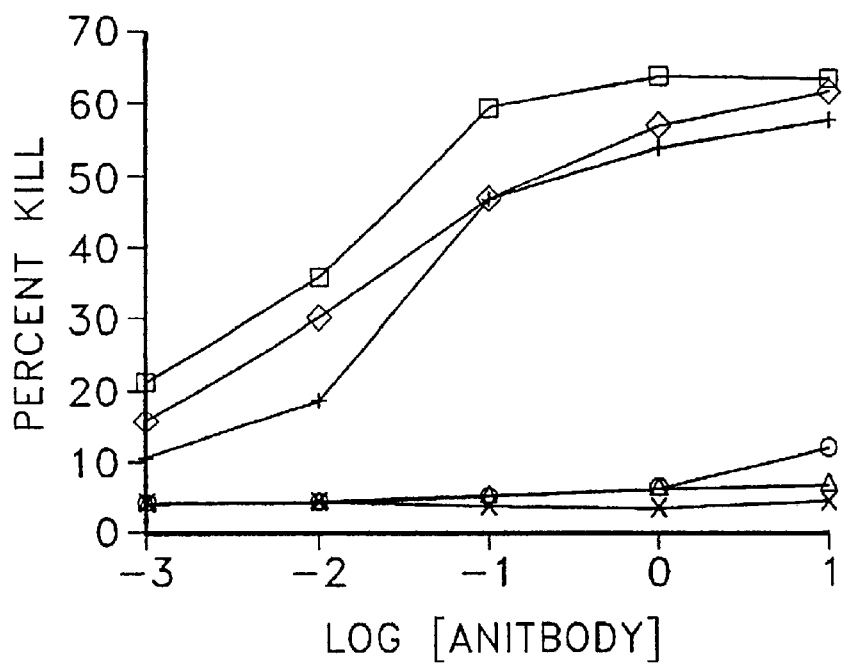
FIG. 10C is a line graph of the ADCC characteristics of H2981 tumor cells which were labelled for 2 h with $^{51}$Cr, washed, and added to IMDM+10% FBS containing tenfold serial dilutions of antibody derivatives, and human PBL as effector cells at an effector to target ratio of 100:1. Assays were incubated for 4.5 hours, spun, and 100 μl of supernatant was measured for counts released. Percentage kill was calculated as [(mean cpm-mean spontaneous release)/(mean maximal release-mean spontaneous release)]×100. Values represent the means of triplicate cultures (SEM<10%). Legend: Chimeric L6 (open diamond), WTD (open square), DM1 (open triangle), HS1 (plus sign), HS2 ("X" sign), and HS3 (open circle).
Figure 10D:
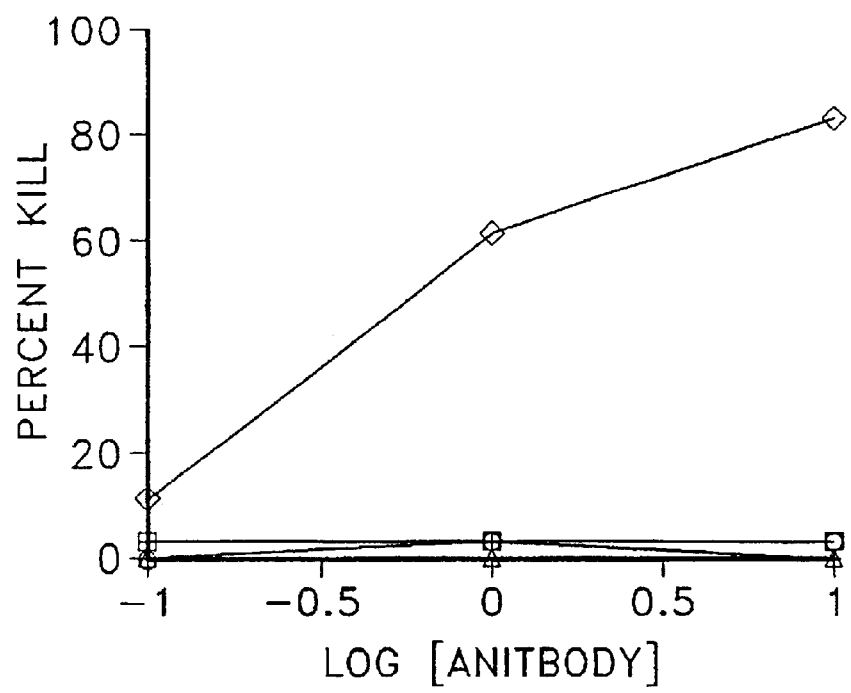
FIG. 10D is a line graph of an assay similar to FIG. 10(C) which was performed to measure complement killing but using complement instead of PBL. Legend: Chimeric L6 (open diamond), WTD (open square), DM1 (open triangle), HS1 (plus sign), HS2 ("X" sign), and HS3 (open circle).

For example, in one embodiment, the monospecific fusion proteins encoded by the vectors of the invention are similar to the single chain antibody in FIG. 9.

In one embodiment of the invention, the expression vector comprises (1) a DNA sequence encoding a first binding domain of an antibody or a cell surface antigen, (2) a DNA sequence encoding a second binding domain of an antibody or a cell surface antigen, (3) a linker encoding a helical peptide which links the DNA sequence encoding the first binding domain and the DNA sequence encoding the second binding domain, and (4) a DNA sequence encoding a molecular tag for detection of the monospecific or bispecific fusion protein.

The molecular tag may be identified by the appropriate molecule which recognizes and binds the molecular tag such as an antibody, a complementary sense or antisense molecule, an enzyme, etc. Examples of molecular tags include an $F_c$ fragment, an HIV fragment, and the hemagglutinin epitope sequence HA1 (Pati et al. (1992) Gene 114 (2):285–8).

In accordance with a preferred embodiment, the expression vector comprises a recombinant bispecific single chain DNA cassette which comprises (1) a DNA sequence encoding a first binding domain of an antibody or a cell surface antigen, (2) a DNA sequence encoding a second binding domain of an antibody or a cell surface antigen, and (3) a linker encoding a helical peptide which links the DNA sequence encoding the first binding domain and the DNA sequence encoding the second binding domain, each of said domains capable of binding the same or a different target or antigen.

In accordance with the practice of the invention, the first and/or second binding domain may be reactive with a cell surface antigen or leucocyte antigen. Cell surface antigens include, but are not limited to, molecules such as CD3, L6, CD28, CTLA4, CD40 or B7. Thus, the first and/or second binding domain may be reactive with CD3. Also, the first and/or second binding domain may be reactive with L6. Further, the first and/or second binding domain may be reactive with CD28. Additionally, the first and/or second binding domain may be reactive with B7. Further, the first and/or second binding domain may be reactive with CD40.

In a preferred embodiment, the expression vector is designated CC9–2 deposited with the American Tissue Culture Collection (ATCC) in the *E. Coli* plasmid CC9–2 having the L6 $V_L$ leader sequence-CD3 s$F_v$-linker-L6 s$F_v$-immunoglobulin $F_c$ in pCDM8) having ATCC No. 69235. It would be clear to one skilled in the art that any DNA sequence may be used. The only requirement is that the coding sequence of the variable region(s) or molecule to be used must be known so that it may be inserted in the cassette for proper alignment and correct reading frame for expression.

Additionally, an expression vector encoding a bispecific fusion protein is provided which comprises a recombinant bispecific single chain cassette comprising a DNA sequence encoding a variable region(s) of any antibody and a DNA sequence encoding a ligand. Examples of such ligands include but are not limited to B7, CTLA4, CD28, CD40, CD3. Other examples of ligands include any of the leucocyte antigens.

For example, the present invention provides an expression vector encoding a bispecific fusion protein comprising a recombinant bispecific single chain cassette comprising a DNA sequence encoding a domain which is reactive with CD3 and a DNA sequence encoding a domain which is reactive with L6. The first or second binding domain may be reactive with CD3. The first or second binding domain may be reactive with L6.

This invention further provides an expression vector encoding a bispecific fusion protein comprising a recombinant bispecific single chain cassette comprising a DNA sequence encoding a domain which is at least a portion of B7 (e.g., the extracellular portion) and a DNA sequence encoding a domain which is reactive with L6.

This invention additionally provides an expression vector encoding a bispecific fusion protein comprising a recombinant bispecific single chain cassette comprising a DNA sequence encoding a domain which is reactive with CTLA4 and a DNA sequence encoding a domain which is reactive with L6. The first or second binding domain may be reactive with CTLA4. The first or second binding domain may be reactive with L6.

Also, the present invention provides an expression vector encoding a bispecific fusion protein comprising a recombinant bispecific single chain cassette comprising a DNA sequence encoding a domain which is reactive with CD28 and a DNA sequence encoding a domain which is reactive with L6. The first or second binding domain may be reactive with CD28. The first or second binding domain may be reactive with L6.

For example, the present invention provides an expression vector encoding a bispecific fusion protein which comprises a recombinant bispecific single chain cassette comprising a DNA sequence encoding a domain which is reactive with CD3 and a DNA sequence encoding the extracellular portion of B7.

Methods for producing expression vectors and the biologically active bispecific fusion proteins according to the present invention are provided. In general these methods comprise (1) isolating mRNA from a B cell hybridoma or other cultured cell synthesizing an antibody or other binding protein; (2) synthesizing cDNA by reverse transcription; (3) cloning binding domains such as the variable region(s) using anchor-tailed oligonucleotides or degenerate oligonucleotides as PCR primers; (4) sequencing the variable region(s) so cloned; (5) constructing gene fusions between variable region genes; (6) inserting the variable region(s) so constructed into a pUCIg vector (or other suitable vectors) cut with SalI and BclI; (7) screening clones for proper fragment configuration and sequencing such clones; (8) transferring the clones into a suitable expression vector such as pCDM8 or piLNXAn; (9) transfecting COS cells by a technique such as the DEAE-Dextran technique; (10) incubating the cells so transfected for a time sufficient for fusion proteins to be expressed, typically about 72 hours; and (11) screening such cells by FACS using FITC goat anti-human IgG and/or ELISA for the production of biologically active bispecific fusion protein.

B. METHODS FOR PRODUCING THE BIOLOGICALLY ACTIVE BISPECIFIC FUSION PROTEIN

A method for producing a biologically active bispecific fusion protein is provided. This method comprises culturing the cells so transfected with the expression vector of the present invention so as to produce the bispecific fusion protein and recovering the protein so produced.

This invention further provides a method for producing a biologically active bispecific fusion protein in a mammalian cell. This method comprises (a) transfecting the mammalian cell with the expression vector of the invention; (b) culturing the mammalian cell so transfected in step (a); and (c) recovering the biologically active bispecific fusion protein so produced by the cultured mammalian cell.

The method for recovering the biologically active bispecific fusion protein comprises: (a) identifying the biologically active bispecific fusion protein by the presence of the molecular tag; and (b) separating the biologically active bispecific fusion protein having the molecular tag so identified from molecules without the molecular tag, so as to recover the biologically active bispecific fusion protein so produced by the cultured mammalian cell.

Although in the examples which follow cells of mammalian origin are used, in principle, any eucaryotic cell is useful in the practice of the subject invention. Examples include human cells, for example fibroblast cells, and cells from other animals such as ovine, porcine, murine, bovine. Specific examples of mammalian cells include COS, HeLa, CHO, DUX, B11, Sp2/0, W138, DHK, and HEPG2 cells.

It would be clear that the biologically active bispecific fusion proteins may be linked to detectable markers and therapeutic agents for use in diagnosis, both in vivo and in vitro, and for use in therapy. Among the detectable markers to which such biologically active bispecific fusion proteins can be linked are enzymes, paramagnetic ions or compounds, members of the avidin-biotin specific binding pair, fluorophores, chromophores, chemiluminophores, heavy metals, and radioisotopes. Among the therapeutic agents to which the biologically active bispecific fusion proteins can be linked are antineoplastic agents, lymphokines, and toxins.

C. CELLS TRANSFECTED WITH THE EXPRESSION VECTORS OF THE INVENTION

Introduction of the expression vector into mammalian cells may be effected by calcium phosphate transfection (Graham and Vander Eb. (1973) Virol. 52:456–467), DEAE-dextran transfection (Lopata, M. A. et al., (1984) Nucl. Acids Res. 12:5707), and electroporation (Potter, H. et al. (1984) PNAS 81:7161). The choice of transfection method depends in part on what type of transfection is to be performed. Both electroporation and $CaPO_4$ transfection can be used to efficiently produce cell lines containing stably integrated DNA. Electroporation is most easily done using suspension cultures, while $CaPO_4$ transfection is most easily done using adherent cells. DEAE-dextran transfection does not work well when producing stable cell lines, but is more reproducible than $CaPO_4$ transfections when used in transient protocols. Other transfection methods are also known in the art.

The expression vectors and novel proteins produced by the methods described herein are not limited to the variable regions set forth hereinabove but are generally applicable to the construction, expression, and screening of any single chain bispecific fusion protein.

D. USES OF THE FUSION PROTEINS ENCODED BY VECTORS OF THE INVENTION

The anti-L6 and anti-CD3 single chain derivatives lacking molecular tags may be useful in therapy or diagnosis for treatment or detection of L6 or CD3 associated diseases. For example, the L6sFv could be chemically attached to a radionuclide for detection or genetically fused to a toxin such as PE40 for therapy.

Because smaller sFv fragments are better able to penetrate tumor mass and have shown improved localization at tumor sites, smaller doses of L6sFv may be effective in targeting therapeutic agents to tumor cells that express high levels of L6 antigen (Colcher, D., Bird, R., Roselli, M., Hardman, K. D., Johnson, S., Pope, S., Dodd, S. W., Pantoliano, M. W., Milenic, D. E., Schlom, J. (1990) In vivo tumor targeting of a recombinant single-chain antigen-binding protein. J. Nat. Cancer Inst. 82:1191–1197; Yokota, T., Milenic, D. E., Whitlow, M., Schlom, J. (1992) Rapid tumor penetration of a single-chain Fv and comparison with other immunoglobulin forms. Cancer Res. 52:3402–3408).

The CD3sFv may well be suited for induction of immunosuppression in vivo since delivery of a T cell receptor signal in the absence of a second signal such as ligation of CD28 can lead to T cell anergy. It has been demonstrated that F(ab')2 fragments of OKT3 are immunosuppressive while markedly reducing the cytokine toxicity associated with whole antibody OKT3-induced immunosuppression (Woodle, E. S., Thistlethwaithe, J. R., Ghobrial, I. A., Jolliffe, L. K., Stuart, F. P., Bluestone, J. A. (1991) OKT3 F(ab')2 fragments: retention of the immunosuppressive properties of whole antibody with marked reduction in T cell activation and lymphokine release. Transplantation 52:354–360).

Interestingly, the CD3 single chain monospecific antibody derivatives exhibited functional properties distinct from native antibody. The CD3Fv-Ig derivative potently induced tyrosine phosphorylation of PLCγ1 and increased the association of PLCγ1 with pp35/36 in comparison to native anti-CD3 mAb. This association has been shown to increase as T cells are maximally stimulated (Kanner, S. B., Deans, J. P., Ledbetter, J. A. (1992a) Regulation of CD3-induced phospholipase C-γ1 (PLCγ1) tyrosine phosphorylation by CD4 and CD45 receptors. Immunology 75:441–447; Kanner, S. B., Ledbetter, J. A. (1992b) CD45 regulates TCR-induced signalling through tyrosine phosphorylation of phospholipase Cγ1. Biochem. Soc. Trans. 20:178–184). Additionally, stimulation of T cells with CD3Fv-Ig resulted in greater overall tyrosine phosphorylation of cellular pro- 'teins following activation. It is possible that because the molecules are smaller than the native mAb, the binding domain on CD3-ε is more accessible and improves the interaction with TCR/CD3-associated tyrosine kinases.

In animal models and in clinical trials in humans, anti-TCR or anti-CD3 mAb have shown enhancement of T cell responses against target cells when crosslinked to target cell antigens. Heteroconjugated or bispecific mAb direct the activity of cytotoxic T lymphocytes or of lymphocyte activated killer cells to kill malignant target cells (Staerz et al., 1986a; Perez et al., 1985a; Perez, P., Hoffman, R. W., Titus, J. A., Segal, D. M. (1986) Specific targeting of human peripheral blood T cells by heteroaggregates containing anti-T3 crosslinked to anti-target cell antibodies. J. Exp. Med. 163:166–178; Liu et al., 1985a; Staerz et al., 1986b) or virally infected target cells (Paya, C. V., McKean, D. J., Segal, D. M., Schoon, R. A., Schowalter, S. D., Leibson, P. J. (1989) Heteroconjugate antibodies enhance cell-mediated anti-herpes simplex virus immunity. J. Immunol. 142:666–671; Zarling, J. M., Moran, P. A., Grosmaire, L. S., McClure, J., Shriver, K., Ledbetter, J. A. (1988) Lysis of cells infected with HIV-1 by human lymphocytes targeted with monoclonal antibody heteroconjugates. J. Immunol. 140:2609–2613; Voss, L. M., David, C. S., Showalter, S. D., Paya, C. V., Liebson, P. J. (1992) Heteroconjugate antibodies enhance cell-mediated anti-herpes simplex virus immunity in vivo. Int. Immunol. 4:417–420).

Although anti-CD3 mAb can induce potent cytokine toxicity in vivo (Abramowicz, D., Schandene, L., Goldman, M., Crusiaux, A., Vereerstraeten, P., De Pauw, L., Wybran, J., Kinnaert, P., Dupont, E., Toussaint, C. (1989) Release of tumor necrosis factor, interleukin-2, and gamma interferon in serum after injection of OKT3 monoclonal antibody in kidney transplant recipients. Transplantation 47:606–608), patients treated with bispecific mAb have not developed cytokine toxicity because their T cells were pretreated with the reagent in vitro and then readministered (Mezzanzanica, D., Canevari, S., Colnaghi, M. I. (1991) Retargeting of human lymphocytes against human ovarian carcinoma cells by bispecific antibodies: from laboratory to clinic. Int. J. Clin. Lab. Res. 21:159–164; Nitta, T., Sato, K., Yagita, H., Okumura, K., Ishii, S. (1990) Preliminary trial of specific targeting therapy against malignant glioma. Lancet 335:368–371). In murine models, molecules smaller than native mAb such as F(ab')2 fragments show increased tumor localization for both monospecific anti-tumor and for bispecific anti-CD3, anti-tumor specificities (van Dijk, J., Zegveld, S. T., Fleuren, G. J., Warnaar, S. O. (1991) Localization of monoclonal antibody G250 and bispecific monoclonal antibody CD3/G250 in human renal cell carcinoma xenografts: relative effects of size and affinity. Int. J. Cancer 48:738–743; Nelson, H., Ramsey, P. S., Kerr, L. A., McKean, D. J., Donohue, J. H. (1990) Regional and systemic distribution of anti-tumor x anti-CD3 heteroconjugate antibodies and cultured human peripheral blood lymphocytes in a human colon cancer xenograft. J. Immunol. 145:3507–3515).

The CD3-L6FvIg molecule may be useful as a novel molecule for mammalian cancer therapy, e.g., human cancer therapy. The molecule contains binding specificity for both CD3 and the tumor antigen L6, and has been shown in vitro to induce T cell proliferation in the presence of L6-positive tumor cells, and to direct CTL killing toward these cells. The two different binding specificities are attached to the hinge, CH2 and CH3 domains of human IgG1, initially to serve as a tag for characterization and purification of the bispecific molecules. This tag is itself a relatively small domain (about 50 kDa) that retains the overall smaller size of the tagged bispecific protein to approximately two-thirds the size of native IgG. Since the tag is of human origin, the overall immunogenicity of the molecule would be expected to be significantly less than whole murine IgG. Additional modifications could be carried out to decrease further the immunogenicity of the bispecific proteins such as humanizing the framework regions and constructing the solvent-accessible portion of the helical linker to resemble helices from known human proteins. Although the Ig portion served as an affinity tail, it may also increase the half-life of the bispecific protein in vivo.

In one report, chimeric mouse anti-colorectal cancer mAb variable regions fused to human IgG1 constant region (Steplewski, Z., Sun, L. K., Sherman, C. W., Ghrayeb, J., Daddona, P., Koprowski, H. (1988) Biological activity of human-mouse IgG1, IgG2, IgG3, and IgG4 chimeric monoclonal antibodies with antitumor activity. Proc. Natl. Acad. Sci. USA 85:4852–4856) administered to ten patients with metastatic colon cancer showed a six-fold increase in circulation time (LoBuglio, A. F., Wheeler, R. H., Trang, J., Haynes, A., Rogers, K., Harvey, E. B., Sun, L., Ghrayeb, J., Khazaeli, M. B. (1989) Mouse/human chimeric monoclonal antibody in man: kinetics and immune response. Proc. Natl. Acad. Sci. USA 86:4220–4224).

Additionally, the Ig-tail used in our bispecific fusion protein is mutated in the CH2 domain (proline to serine at residue 238). This mutation ablates ADCC activity mediated by the interaction of the human IgG1 tail with Fc receptors. This should prevent "reciprocal" killing between CD3-positive T cells and Fc-receptor-bearing cell in vivo (Clark et al., 1987a). Finally, although the bispecific molecule is expressed from transient transfection of COS cells, the protein may be potentially expressed in a stable transfection system.

The following fusion proteins are contemplated. A fusion protein that mediates antibody dependent cellular cytotoxicity comprising an extracellular domain of a CTLA4 molecule that binds a B7 antigen and a portion of a modified immunoglobulin molecule which mediates antibody dependent cellular cytotoxicity, wherein the modified immunoglobulin molecule has a 0H2 domain comprising amino acids 18–30 of SEQ ID NO:21, wherein leucine at position 21 is replaced with phenylalanine.

A fusion protein that mediates antibody dependent cellular cytotoxicity comprising an extracellular domain of a CTLA4 molecule that binds a B7 antigen and a portion of a modified immunoglobulin molecule which mediates antibody dependent cellular cytotoxicity, wherein the modified immunoglobulin molecule has a CH2 domain comprising amino acids 18–30 of SEQ ID NO:21, wherein leucine at position 22 is replaced with glutamate.

A fusion protein that mediates antibody dependent cellular cytotoxicity comprising an extracellular domain of CTLA4 molecule that binds a B7 antigen and a portion of a modified immunoglobulin molecule, wherein the modified immunoglobulin molecule has a CH2 domain comprising amino acids 18–30 of SEQ ID NO:21, wherein glycine at position 24 is replaced with alanine.

A fusion protein that mediates antibody dependent cellular cytotoxicity comprising an extracellular domain of CTLA4 molecule that binds a B7 antigen and a portion of a modified immunoglobulin molecule, wherein the modified immunoglobulin molecule has a CH2 domain comprising amino acids 18–30 of SEQ ID NO:21, wherein proline at position 25 is replaced with serine.

A fusion protein that mediates antibody dependent cellular cytotoxicity comprising an extracellular domain of CTLA4 molecule that binds a B7 antigen and a portion of a modified immunoglobulin molecule which mediates antibody dependent cellular cytotoxicity, wherein the modified immunoglobulin molecule has a CH2 domain comprising amino acids: 18–30 of SEQ ID NO:20, 18–30 of SEQ ID NO:22 or 18–30 of SEQ ID NO:23.

A fusion protein that mediates antibody dependent cellular cytotoxicity comprising an extracellular domain of CTLA4 molecule that binds a B7 antigen and a portion of a modified immunoglobulin molecule, wherein the modified immunoglobulin molecule has a hinge and CH2 domains comprising amino acids: 3–30 of SEQ ID NO:20, 3–30 of SEQ ID NO:22 or 3–30 of SEQ ID NO:23.

ADVANTAGES OF THE INVENTION

The subject invention overcomes the problems associated with current methodologies of antibody production.

To circumvent problems encountered by others in producing a bispecific fusion protein, we adapted an existing COS cell expression system to achieve secretion of functional single chain antibody derivatives from recombinant bispecific single chain cassette DNA. Single chain antibodies were constructed by fusing the Fc domain of human IgG1 to the variable regions for murine antibodies against human antigens (e.g., CD3 and L6). The Fc region served as a convenient molecular tag sequence for identification and purification of fusion proteins with varying specificities. Additionally, effector functions conferred by this segment of the antibody may be useful for certain therapeutic applications.

Unlike bacterial expression systems where recovery of biologically active molecules is problematic, even for molecules possessing a single binding specificity, the present invention provides transient expression from COS cells which yield culture supernatants containing the expressed biologically active fusion proteins which could then be purified by conventional affinity chromatography. Interestingly, the single chain bispecific fusion protein molecules so produced exhibit properties that were distinct from the parent antibodies.

We chose mammalian expression of these bispecific fusion protein molecules because the recovery of biologically active molecules from bacterial expression systems is problematic, even for molecules possessing only a single binding specificity. With mammalian expression, simple, rapid production of antibody derivatives may be achieved which is important so that characterization, evaluation, and comparison between molecules is possible within a relatively short period of time.

Gene fusions in which individual protein domains are present on interchangeable recombinant bispecific single chain cassette DNA create the potential for generating novel combinations, making rapid exchanges, and screening different domains for their efficacy in performing a desired function. Expression of the constructs in a transient transfection system is preferable to other methods of production for the initial recombination and screening steps. Only those molecules exhibiting the desired subset of characteristics from this screening would require shuttling into a secondary expression system for large scale production, eliminating lengthy or complicated production and isolation procedures for the majority of molecules generated.

We set out to develop a system for rapid construction, expression, and analysis of antibody binding sites assembled into larger molecules as recombinant bispecific single chain DNA cassettes having interchangeable DNA cassettes, i.e. DNA cassettes encoding single chain variable regions or other binding domains that can be exchanged for another. The sequences of the first and second binding domains are replaceable or interchangable. Different sequences may replace existing ones.

Unlike previously-described constructs, the bispecific single chain cassettes are versatile since any variable regions may be placed in any or both of the first or second binding domains.

By constructing novel combinations of antibody structural domains, for example molecules which couple two unrelated binding specificities and the desired effector functions might be produced which exhibit improved therapeutic potential. Such bispecific single chain antibody derivatives serve as adaptor molecules for two non-interacting cell surface receptors to create an artificial receptor-ligand pair.

The data herein suggest that the bispecific fusion protein molecules so expressed from a recombinant bispecific single chain DNA cassette may be capable of targeting a cytotoxic response by T cells against human tumors expressing L6 in vivo as well as in vitro, without the need for extensive tissue culture manipulations or purification away from potentially toxic monospecific antibodies against CD3.

Single chain antibody derivatives which couple the specificities for tumor cell binding and T cell binding and activation provide a significant improvement over single monoclonal antibody based therapies for human disease. The approach described here for the design, construction, expression, and testing of gene fusions is a versatile one which offers significant advantages in rapidity, simplicity, and reproducibility for testing novel combinations between the functional domains of unrelated molecules for their ability to function together within a single molecule in the desired manner.

This invention is illustrated in the Example which follows. This section is set forth to aid in understanding the invention but is not intended to, and should not be construed to, limit in any way the invention as set forth in the claims which follow.

EXAMPLE 1

Materials and Methods

Modification of Expression Vectors: The plasmids pCDM8 and piLNXAn were modified by replacing the stuffer fragment with several smaller stuffer fragments, each of which confers some functional property to the resulting fusion protein.

The mammalian expression vector is diagrammed with the alterations and additions made shown along the top portion of the vector. Expression of fusion cassettes is driven by the CMV promoter, and replication in bacteria and mammalian cells is achieved by the appropriate origins indicated at the bottom of the vector. The vector contains the supp gene to suppress nonsense mutations in the ampicillin and tetracycline genes present in the p3 plasmid in the appropriate host bacterial strains. The termination and poly A addition signals are provided by the appropriate regions from SV40.

The HindIII site at the 5' end of the stuffer region was used to insert a HindIII-SalI cassette containing a leader sequence for secretion of fusion proteins obtained from the light chain variable regions of the anti-L6 antibody (also referred to herein as anti-L6) (FIG. 1). This sequence was encoded on complementary 72-mer oligonucleotides with HindIII and SalI cohesive end overhangs. The sense oligonucleotide used was L6VL-LP5/AGC TTA TGG ATT TTC AAG TGC AGA TTT TCA GCT TCC TGC TAA TCA GTG CTT CAG TCA TAA TGT CCA GAG GAG (SEQ. ID NO: 1) while the complementary oligonucleotide was L6VL-LP3/TCG ACT CCT CTG GAC ATT ATG ACT GAA GCA CTG ATT AGC AGG AAG CTG AAA ATC TGC ACT TGA AAA TCC ATA (SEQ ID NO: 2). The sense oligonucleotide was phosphorylated with polynucleotide kinase (Boehringer-Mannheim, Indianapolis, Ind.) and annealed to the complement prior to ligation according to previously published procedures (Sambrook, J., Fritsch, E. F., Maniatis, T. (1989) Molecular cloning - a laboratory manual, second edition. ISBN 0-87969-309-6). Only one of the oligonucleotides was kinased to prevent multiple tandem insertions.

In addition, the XbaI site at the 3' end of the stuffer fragment was used to insert a molecular tag or a simple stop codon flanked by BclI and XbaI restriction sites at the carboxyl terminus (FIG. 1). The molecular tags tested included an Fc fragment from human IgG1, a human immunodeficiency virus (HIV) peptide from the V3 loop of gp110, a FLAG peptide, and the constant region domain of human C-kappa. The human IgG1 sequences were isolated from the RNA of the chimeric L6 transfectoma by coupled reverse transcription (Avian myeloblastosis virus; Life Sciences, St. Petersburg, Fla.) and/or PCR reactions from the RNA of a myeloma expressing human-mouse chimeric L6. Several different mutant derivatives of the Fc domain were constructed from PCR reactions using forward primers containing the appropriate mutations in either the hinge or the CH2 region.

The modified expression vectors were tested by insertion and expression of the variable regions for two different antibody binding specificities, the human L6 tumor antigen and human CD3-ε. The single chain antibody derivatives bound antigen with varying avidities and affinities, depending on the molecular tag to which they were fused. The Fc domain of human IgG1 was the most successful tag at reproducing the binding characteristics of the native antibody, despite the absence of CH1 and Cκ domains. Several other tags were constructed and tested, but the Cκ (Traunecker, A., Lanzavecchia, A. M., Karjalainen, K. (1991) Bispecific single chain molecules (Janusins) target cytotoxic lymphocytes on HIV infected cells. EMBO J. 10: 3655–3659) and FLAG peptides both failed to function reliably. The peptide RKSIRIQRGPGRAFVTIGKI (SEQ ID NO: 3) from the V3 loop of gp110 encoded by human immunodeficiency virus was also used as an affinity tail, recognized by the peptide-specific mAb 110.3. This tag gave variable results depending on the Fv to which it was fused, failing to function properly when fused to L6, but performing successfully when fused to CD3.

The peptide 29 (RKSIRIQRGPGRAFVTIGKI) (SEQ ID NO: 3) corresponds to a segment of the V3 loop of gp 110 from HIV (HIV peptide). A molecular tag was created by annealing two complementary 76-mer oligonucleotides with cohesive end overhangs. The sense oligonucleotide included a Bcl I overhang, the V3 loop sequences, and a stop codon HIVSTOP5 GA TCA AGA TCC GCG GAA ATC GAT TAG AAT CCA GAG AGG CCC TGG GCG CGC CTT CGT TAC GAT CGG CAA GAT CTA GT (SEQ ID NO: 4), while the complementary primer contained the XbaI overhang HIVSTOP3/CTA GAC TAG ATC TTG CCG ATC GTA ACG AAG GCG CGC CCA GGG CCT CTC TGG ATT CTA ATC GAT TTC CGC GGA TCT T (SEQ ID NO: 5). The sense oligonucleotide was phosphorylated and annealed to the unphosphorylated reverse primer prior to ligation into BclI-XbaI digested vector as described above.

We tested whether the FLAG peptide marketed by IBI for use as an amino-terminal tag would still work when placed at the carboxyl end of the tagged protein. Complementary oligonucleotides were designed containing the following 51-mer sequences:FLAG5/GAT CAA GAC TAC AAG GAC GAC GAT GAC AAG TGA GCG GCC GCG AAT TCG TCT (SEQ ID NO: 6) and FLAG3/CTA GAG ACG AAT TCG CGG CCG CTC ACT TGT CAT CGT CGT CCT TGT AGT CTT (SEQ ID NO: 6). These sequences were kinased, annealed, and ligated into the vector distal to the antibody binding domain. The human C-kappa sequences were obtained by reverse transcription and PCR from the chimeric L6 RNA as described previously. The forward primer for isolation of C-kappa was L6CK5BCL/GGT GCT CTG ATC ACT GTG GCT GCA CCA TCT GTC TTC ATC (SEQ ID NO: 8), and the reverse primer was L6CK3XBA/ CCT CCT CAT TCT AGA CTA ACA CTC TCC CCT GTT GAA GCT (SEQ ID NO: 9).

The helical peptide linker used to make a recombinant bispecific single chain cassette DNA between the CD3 and L6 binding domains was encoded on complementary 78-mer oligonucleotides with GATC cohesive end overhangs. The sense oligonucleotide is Fvlink/GAT CAA TCC AAC TCT GAA GAA GCA AAG AAA GAG GAG GCC AAA AAG GAG GAA GCC AAG AAT CTA ACA GCC TCG AGA GC (SEQ ID NO: 10), and the antisense oligonucleotide is Fvlink2/GAT CGC TCT CGA GGC TGT TAG ATT TCT TGG CTT CCT CCT TTT TGG CCT CCT CTT TCT TTG CTT CTT CAG AGT TGG ATT (SEQ ID NO: 11). The peptide encoded is hydrophilic with an abundance of charged amino acids (DQSNSEEAKKEEAKKEEAKKSNSLESL) (SEQ ID NO: 12) to increase the solubility of the molecule. The sequence motif $(EEAKK)_n$, residues 6–10 of SEQ ID NO:12 is particularly hydrophilic due to an abundance of charged amino acids.

PCR reactions (in a 100 μl total reaction volume) were run in Taq polymerase buffer (Stratagene, Torrey Pines, Calif. or Boehringer-Mannheim), with 20 μmol each dNTP, 50–100 pmol primers, 1–10 ng template, and Taq polymerase (Stratagene or Boehringer-Mannheim). Reactions were performed using a Perkin-Elmer Cetus Thermal Cycler with a 30-cycle program, typically consisting of steps of 1 minute at 94° C., 1 minute at 55° C., and 1 minute at 72° C. Ligation products were transformed into MC1061/p3 and colonies were screened for the appropriate insertion plasmids. Positive clones were verified by DNA sequencing and mini-transfection.

Isolation of V regions: RNA from the chimeric L6 transfectoma was isolated using the rapid NP-40 lysis technique and full-length DNA for both heavy and light chain were amplified by using primers identical to the published sequences for L6 and human constant regions (Hieter, P. S., Maz, E. E., Seidman, J. G., Maizel, J. V. Jr., Leder, P. (1980) Cloned human and mouse kappa immunoglobulin constant and J region genes conserve homology in functional segments. Cell 22:197–207; Liu et al. (1987) Proc. Natl. Acad. Sci. USA 84:3438–3442) but with restriction sites attached for cloning. These full-length cDNAs were used as template for secondary PCR reactions to subclone variable regions. In one example, subfragments from the variable regions were cloned by PCR from cDNA templates generated with random hexamers rather than specific primers.

RNA from G19-4 cells was extracted using the rapid NP-40 lysis technique. The $V_L$ and $V_H$ sequences of the anti-CD3 hybridoma G19-4 were amplified by using established PCR methods (Orlandi, R., Gussow, D. H., Jones, P. T., Winter, G. (1989) Cloning immunoglobulin variable regions for expression by the Polymerase Chain Reaction.

Proc. Nat. Acad. Sci. 86:3833–3837). First strand cDNA synthesis was performed using AMV reverse transcriptase (Life Sciences) and primers complementary to the constant regions of the heavy or light chains. First strand cDNA products were tailed with poly-G using terminal transferase (Stratagene, Torrey Pines, Calif.). PCR was then performed using 100 pmol of each primer and 1–2 μl purified G-tailed cDNA gene-cleaned cDNA from the first strand synthesis. The ANCTAIL forward primer contained nonsense DNA and poly-C sequences complementary to the anchor sequence, the ANC-ER forward primer contained an EcoRI site and nonsense sequences upstream of the anchor site, and the MHγC and MCK-3 reverse primers contained sequences internal to the first-strand primer, complementary to the constant regions of the heavy and light chains, respectively.

Primer sequences were as follows:

| | | |
|---|---|---|
| ANCTAIL: | 5'-GCATGTGCAAGTCCGATGAGTCCCCCCCCCCCCCC-3' | (SEQ ID NO: 13), |
| ANC-ER: | 5'-ACGTCGAGAATTCGCATGTGCAAGTCCGATGAGTCC-3' | (SEQ ID NO: 14), |
| MHγC: | 5'-A(TC)CTCCACACACAGG(AG)(AG)CCAGTGGATAGAC-3' | (SEQ ID NO: 15), |
| MCK-1: | 5'-CTTCCACTTGACATTGATGTCTTTG-3' | (SEQ ID NO: 16), |
| MCK-3: | 5'-CAAGAAGCACACGACTGAGGCA-3' | (SEQ ID NO: 17). |

Immunostaining and FACS Analysis: Jurkat cells, peripheral blood lymphocytes, and/or L6 positive tumor cells (H2981 or H3639) were analyzed by indirect immunostaining. Before staining, H2981 cells were detached from flasks by incubation in trypsin-EDTA (GIBCO-BRL). Cells were incubated with single chain antibody or native parent antibody at various concentrations in binding buffer (GIBCO-BRL), for 40 minutes at 4° C. Cells were washed after the first step and incubated with a FITC-conjugated second step reagent for an additional 30–40 minutes at 4° C. Second step antibody was one of the following: goat anti-mouse Ig for murine mAbs, goat anti-human IgG for single Ig fusions (Tago, Inc., Burlingame, Calif.), FITC-110.3 directed against the V3 loop of gp110 for HIV peptide fusions, and FITC-α idiotype (1B) against the L6 antibody for all types of L6 containing constructs. Fluorescence was analyzed on a FACS IV cell sorter (Becton Dickenson and Co., Mountain View, Calif.) equipped with a four decade logarithmic amplifier.

Competition assays were performed by mixing the two antibodies together at varying ratios to total 10 μg/ml antibody prior to addition of cells. One of the two antibodies was labelled with FITC, usually chimeric or murine L6, or native G19-4. For inhibition assays, the first antibody was added 30 minutes prior to addition of the second FITC-conjugated antibody.

Cell Culture, Transfections, and Purification of Fusion Proteins: COS cells were transfected with expression plasmids as previously described (Linsley, P. S., Brady, W., Grosmaire, L., Aruffo, A., Damle, N. K., Ledbetter, J. A. (1991) Binding of the B cell activation antigen B7 to CD28 costimulates T cell proliferation and interleukin 2 mRNA accumulation. J. Exp Med. 173:721–730; Aruffo and Seed, 1987a). Plasmid DNA was added to transfection media at 1 μg/ml in a total volume of 12 ml/150 mm plate. Spent serum free culture media from three collections of transfected COS cells was pooled and used for purifying fusion proteins containing Ig, HIV, or STOP molecular tags. Cellular debris was removed by low-speed centrifugation and supernatants were sometimes filtered through 0.2 μm filters prior to purification. Media from Ig fusion transfections was applied to a column of immobilized protein A (Repligen Corp., Cambridge, Mass.) equilibrated with 0.05 M sodium citrate, pH 8.0 (Linsley et al., 1991a). For 500 ml of supernatant, 1 ml of packed bed volume protein A was used. After two applications of media, the column was washed with 100 mM potassium phosphate, pH 8.0, and bound protein was eluted with 0.05 M sodium citrate, pH3. Fractions were collected into tubes containing ⅕ volume 1 M Tris pH 8.0. Fractions containing the peak of $A_{230}$ absorbing material were pooled and dialyzed against PBS before use. Protein concentration was determined using the BioRad protein assay kit based on the Lowry technique.

For fusion proteins containing other molecular tags, affinity columns were made by immobilizing appropriate antibodies (either anti-L6 idiotype mAb 13B or anti-HIV mAb 110.3 directed against the V3 loop of gp 110) using CNBr-activated Sepharose 4B according to the instructions from Pharmacia. The affinity matrices contained approximately 5 mg mAb per ml of bed volume and the typical column size was 1×5 cm (4 ml). Samples were adjusted to pH7 and applied to the appropriate immunoaffinity column that had been previously washed with 0.1 M citric acid, pH 2.2 and equilibrated in PBS, pH 7.2. The column was washed thoroughly with PBS and the bound material was eluted with 0.1 M citrate pH 3.0, followed by immediate neutralization with Tris. Purified antibody derivative was finally dialyzed into PBS and sterile filtered.

Cell Adhesion Assays: Adhesion assays were performed essentially as described (Linsley, P. S., Clark, E. A., Ledbetter, J. A. (1990) T-cell antigen CD28 mediates adhesion with B cells by interacting with activation antigen B7/BB1. Proc. Natl. Acad. Sci. USA 87:5031–5035), in the presence of 10 mM EDTA. Jurkat cells were first labeled with $^{51}Cr$ and incubated with antibody stimuli, washed, and incubated with H2981 tumor cells and were examined microscopically. To prevent nonspecific binding to H2981 cells, the Jurkats and H2981 monolayers were incubated with an irrelevant antibody to saturate Fc receptors prior to addition of the CD3Ig (also referred to herein as CD3FvIg), L6Ig (also referred to herein as L6FvIg), or CD3-L6Ig (also referred to herein as CD3-L6FvIg) antibody derivatives. After the adhesion reactions were complete, monolayers were washed five times with ice-cold RPMI media, solubilized by addition of 0.5 M NaOH, and radioactivity measured in a gamma counter. Numbers of bound cells were calculated by dividing total bound radioactivity (cpm) by the specific activity (cpm per cell) of labeled cells (FIG. 6).

Figure 6:
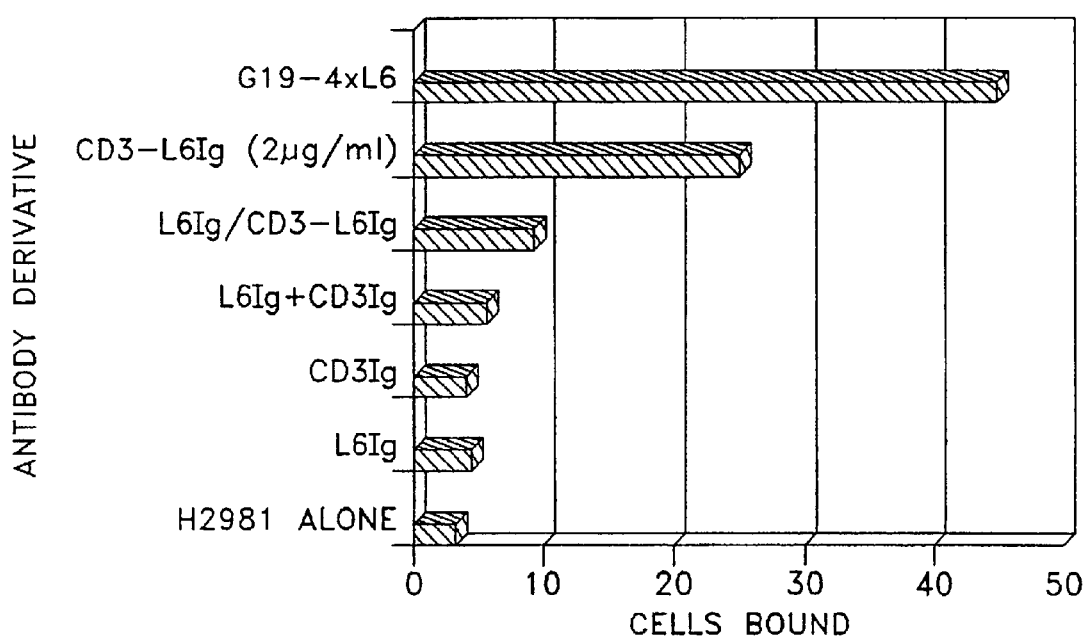
FIG. 6 is a bar graph showing that the bispecific molecule CD3-L6Ig mediates adhesion between H2981 and Jurkat cells and thus is capable of binding to CD3- and L6-expressing cells simultaneously.

In FIG. 6, monolayers of H2981 tumor cells were plated at a density of $10^5$ cells/well in 48 well plates, fixed in 0.1% paraformaldehyde for 20 min at 23° C., washed, blocked in complete RPMI+10% FBS, and preincubated alone or with the antibody indicated for 1 h at 37° C. A heteroconjugate of anti-CD3 (G19-4) and anti-L6 mAb was used as a positive control. All antibodies were used at 20 μg/ml except where indicated. Jurkat cells were labelled with 51 Cr, preincubated in 10 mM EDTA, and added to the tumor cells and antibodies. Adhesion was initiated by spinning the plates at 1000 rpm for 2 min. Reactions were incubated 45 min at 37° C., washed five times in ice cold RPMI, and lysed in 0.5 N NaOH. Counts released were determined by gamma counting. Data represent the number of cells bound (x$10^3$). Mean and standard deviation (error bars) of three replicate determinations are shown.

SDS-PAGE and Western Blotting: Acrylamide gels forming a linear 6–15% gradient with a 4% stacker were run at 225 Volts for 3 hours or overnight at 8 mAmp. Gels were immunoblotted to nitrocellulose membranes using a Western Semi-dry transfer apparatus (Ellard Instruments, Seattle, Wash.) at 130 mAmp for 1 hour. Blots were blocked with 1% nonfat milk, 0.05% NP-40 in PBS (BLOTTO, i.e., blocking buffer) for 1–2 hours. The first antibody incubation was performed with alkaline-phosphatase conjugated goat anti-human IgG (Boehringer-Mannheim) at a 1:1500 dilution in BLOTTO, or with the appropriate dilution of unconjugated murine or chimeric antibody or anti-idiotypic antibody for detection of non-Ig fusions, i.e., $Sf_v$ lacking Ig tags. In any case, blots were washed three times in BLOTTO and incubated with alkaline phosphatase conjugated goat anti mouse or anti human IgG if a second step was required. Blots were developed in Western Blue (Promega, Madison, Wis.) for 5–15 minutes, and the reaction stopped in distilled water.

Immunoprecipitation and western blotting with anti-p-tyr: Jurkat T cells were unstimulated (0) or stimulated with native G19-4 Mab (Ledbetter, J. A., Norris, N. A., Grossmann, A., Grosmaire, L. S., June, C. H., Ucklin, F. M., Cosand, W. L., Rabinovitch P. S. (1989) Enhanced transmembrane signalling activity of monoclonal antibody heteroconjugates suggest molecular interactions between receptors on the T cell surface. Mol. Immunol. 26:137–145) or with CD3Fv-Ig at the concentrations indicated, and were lysed in modified RIPA buffer (Kanner, S. B., Reynolds, A. B., Parsons, J. T. (1989) mmunoaffinity purification of tyrosine-phosphorylated cellular proteins. J. Immunol. Methods 120:115–124) containing phosphatase and protease inhibitors (1 mM sodium orthovanadate, 1 mM PMSF, 2 mM EGTA, 0.5% aprotinin and 10 μg/ml leupeptin). Cell lysates were cleared (10 min at 14000 rpm) and immunoprecipitated with either rabbit anti-p-tyr or PLCγ1 antiserum. Immune complexes were recovered with protein A-Sepharose beads (Pharmacia, Piscataway, N.J.) and washed. The proteins were separated by SDS-PAGE (8%) and were transferred to PVDF Immobilon (Millipore, Bedford, Mass.) for 2 hours at 4° C. The immunoblots were blocked before addition of 0.5 μg/ml of affinity purified rabbit anti-p-tyr in blocking buffer. Proteins were detected with 1 μCi/ml high specific activity $^{125}$I-labelled protein A (ICN Biomedicals, Costa Mesa, Calif.) and autoradiography.

Proliferation Assays: Peripheral blood lymphocytes were isolated by dilution and centrifugation through lymphocyte separation media (Organon Teknika, Durham, N.C.). Lymphocytes were washed several times in serum free RPMI 1640, and cell concentration adjusted to $10^6$ cells/ml in RPMI containing 10% FCS. Cells were cultured in 96-well, flat bottom plates (5x$10^4$ cells/well in a volume of 0.2 ml). Proliferation was measured on triplicate samples by uptake of [$^3$H] thymidine at 1 μCi/ml during the last 6–8 hours of a three day culture. PHA activated T cells were prepared by culturing PBL with 1 μg/ml PHA (Wellcome, Charlotte, N.C.) for 5 days, and resting one day in media lacking PHA.

H2981 tumor cells were irradiated at 10,000 rads prior to use in proliferation assays. Cells were either prebound to fusion proteins and washed before incubating with PBL ("prebound" samples) or were included with fusion proteins in solution ("solution samples") during the three day culture. Washing of the prebound samples removes unbound protein so that only protein bound to the tumor cells contributes to the stimulation of PBL during the assay. PBL were titrated with respect to irradiated cells as follows: (2:1), 5:1, 125:1, (625:1), where the first number refers to the relative number of PBL present (5x104 cells/well) compared to decreasing numbers of tumor cells.

Cytotoxicity Assays: H2981 tumor cells were incubated with [$^{51}$Cr] for two hours prior to incubation with fusion protein (0.1 μg/ml to 10 μg/ml) and PBL (at several effector: target ratios ranging from 10:1 to 100:1). Cells were cultured in RPMI containing 10% FCS in a total volume of 0.2 ml for five hours prior to counting. Chromium release was quantified on a gamma counter to measure cytotoxicity targeted against the tumor cells.

COS cells are capable of expressing antibodies from recombinant bispecific single chain cassette DNA: We set out to develop a system for transient mammalian expression of antibody molecules to facilitate their rapid detection, purification, and characterization. It was important that the system be versatile enough to accommodate molecules of varying specificities and exchanges of domains to simplify the generation, testing, and comparison between different single chain bispecific antibodies. A COS cell transient expression system has been used successfully by previous workers to express soluble cell surface receptors by creating fusion proteins between the extracellular domain of the surface receptor and the heavy chain of human immunoglobulin IgG1 (Aruffo and Seed, 1987b; Linsley et al., 1991b).

This system was chosen as an attractive alternative to bacterial expression systems because the molecules are secreted and could be easily recovered in active form from culture supernatants. Initial experiments examined whether a COS cell transient expression system might be capable of expressing and secreting functional intact IgG molecules using cDNA rather than genomic sequences. Full length kappa and gamma cDNA cassettes encoding anti-tumor antigen L6 specificity were ligated to pCDM8 and the insertion vectors cotransfected into COS cells by the DEAE-Dextran procedure. Culture supernatants were found to contain protein levels ranging from 100–500 ng/ml with binding activity for L6 positive tumor cells, indicating that COS cells were capable of assembling and secreting native antibody from recombinant bispecific single chain cassette DNA.

Adaptation of mammalian expression vectors: Once the ability of COS cells to express such molecules was verified, we modified the expression vectors pCDM8 and piLNXAn to express single chain antibody molecules using interchangeable cassettes encoding individual protein domains. The vectors pCDM8 and piLNX use either the cytomegalovirus or the AMV promoter and enhancer to achieve expression of genes inserted into the polylinker/stuffer region located downstream of the control regions. This region was altered to contain two short cDNA cassettes flanking the variable region insertion site in the polylinker. FIG. 1 diagrams the vector modifications and is a schematic view of the vector modifications and the configuration of variable regions for expressed single chain molecules. A HindIII-SalI fragment containing the leader peptide from the L6 kappa light chain variable region was inserted at the 5' end of the polylinker to achieve secretion of the molecules fused to it. A BclI-Xba fragment encoding the hinge, CH2, and CH3 domains of human IgG1, i.e., a molecular tag, was fused in frame at the 3' end of the polylinker to facilitate detection and purification of molecules with various specificities. Single chain antibody cassette DNA encoding the variable regions of the heavy and light chains were connected to one another by a short peptide linker and inserted as SalI-BclI fragments (other compatible ends were sometimes used) between these two short flanking cassettes so that a single open reading frame was formed. We have thereby adapted existing mammalian expression vectors to achieve efficient expression of CDNA cassettes encoding single chain antibody molecules (SCA) of any specificity. The system permits the rapid expression, purification, screening, and alteration of fusion proteins so that cassettes encoding different molecular tags, linkers, and binding specificities may be compared for their relative effectiveness in expression of functional soluble molecules.

Construction and expression of single chain monospecific L6$F_v$-Ig, CD3 $F_v$-Ig, and bispecific CD3-L6Ig antibody derivatives: Two different binding specificities were used as models to test the adapted single chain antibody expression system. The variable regions for the heavy and light chains of antibodies directed against the L6 tumor antigen and the CD3 T cell surface receptor were isolated as described in Materials and Methods.

The variable regions of anti-L6 or G19-4 were fused into a single coding region by using overlap extension PCR to create a $(Gly_4Ser)_3$ linker between the carboxyl end of $V_L$ and the amino terminus of $V_H$.

Figure 2A:
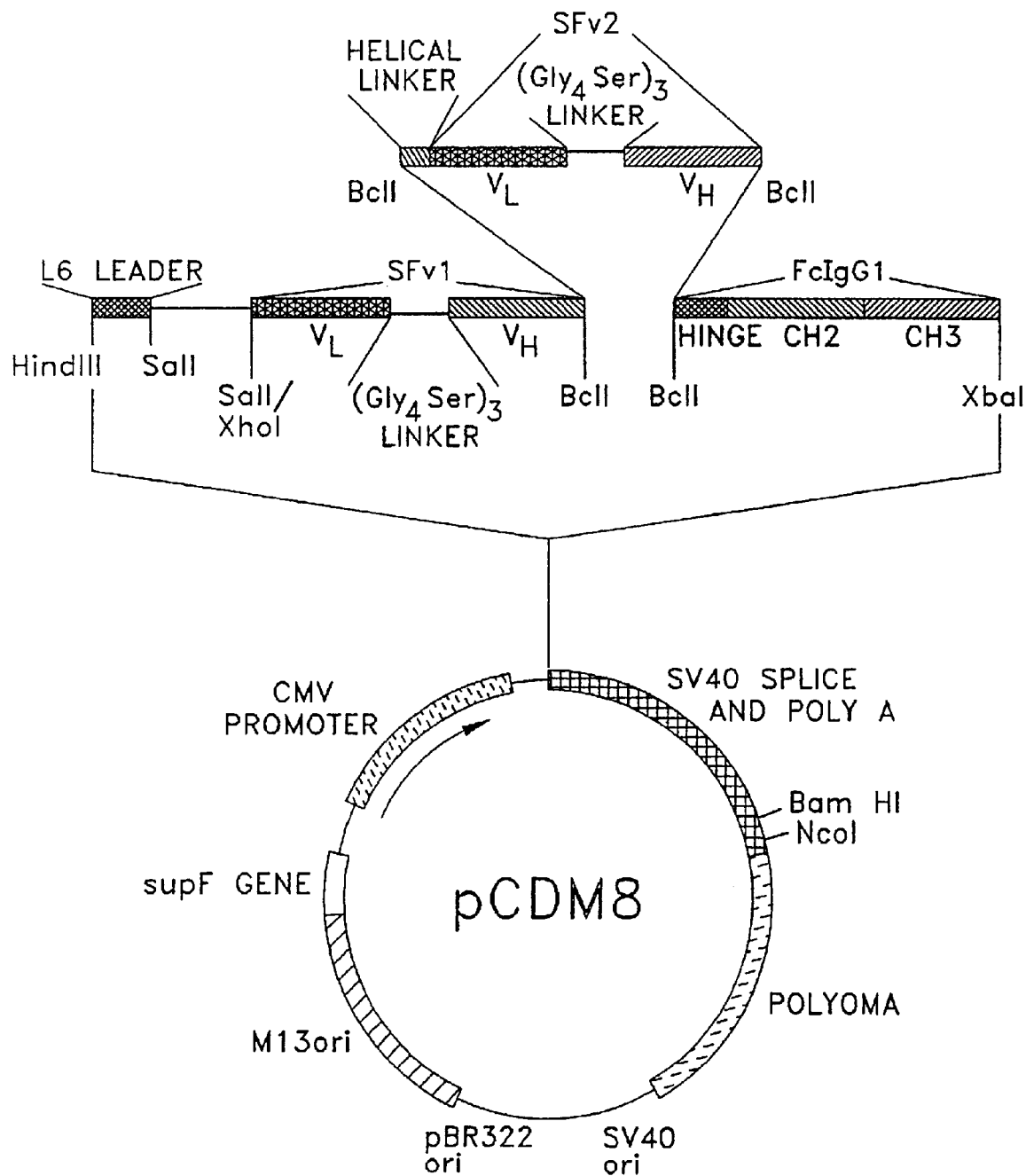
FIG. 2A is a diagram of the pCDM8 expression vector including the recombinant bispecific single chain cassette.

FIG. 2A displays the single open reading frame created by fusion of the light and heavy chain variable region sequences for the G19-4 antibody with the $(Gly_4Ser)3$ linker.

cDNA constructs encoding the leader peptide from the L6 light chain variable region (stippled region), CD3-L6 antigen binding domains (unshaded region), and human IgG1 Fc domain (shaded region) were constructed as described in Materials and Methods (FIG. 2A).

In FIG. 2A the mammalian expression vector pCDM8 was modified by removal of the stuffer fragment and replacement with adaptor sequences for expression of single chain antibody molecules. A HindIII-SalI fragment encoding the leader peptide from the light chain variable region of anti-L6 was inserted to achieve secretion of the expressed molecules. The Fc domain of human IgG1 was included downstream as a BclI-XbaI segment to facilitate detection, purification, and characterization of fusion constructs. A smaller molecular tag sequence encoding a portion of the V3 loop of gp110 from HIV was also used for the CD3 constructs. Between the leader sequence and the tag, a fusion cassette between $V_L$ and $V_H$ was inserted, with the two domains separated by a $(Gly_4Ser)_3$ amino acid linker.

Bispecific molecules could be constructed by inserting a second $V_L$-$V_H$ cassette at the BclI site between the first cassette and the Fc domain. The two binding specificities were separated from one another by an oligonucleotide encoding a 27 amino acid helical peptide linker to prevent steric hindrance and improve solubility.

Sequences displayed show the junctions between each domain, with amino acids introduced during construction indicated in bold face type.

Figure 2B:
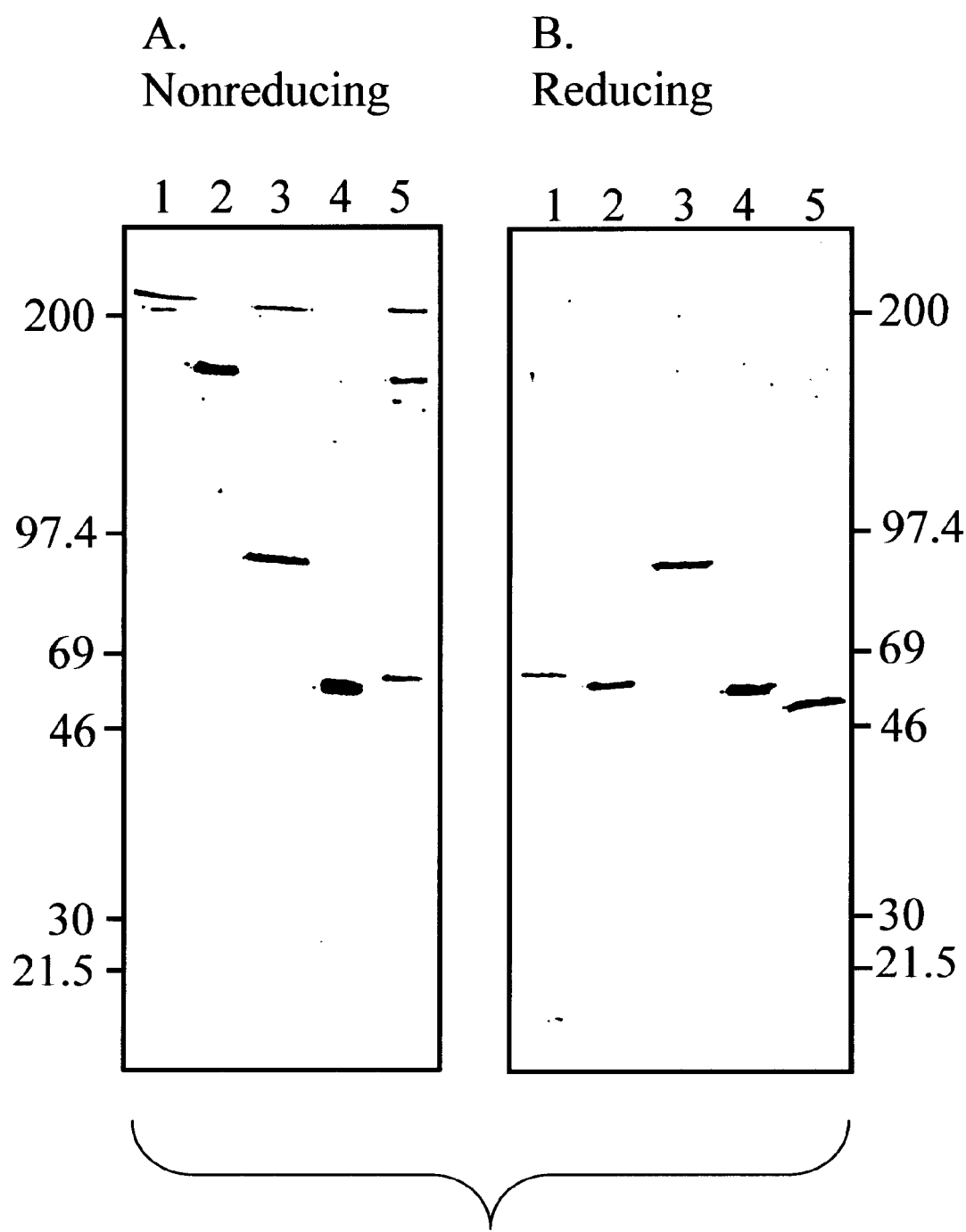
FIG. 2B is a photograph of a western blot of single chain anti-L6, anti-CD3, and anti-CD3-L6 bispecific fusion protein molecules. Serum free spent culture medium from COS cell transfections was collected and purified by protein A affinity chromatography. Protein was resuspended in loading buffer and subjected to SDS-PAGE gradient gel (5–16%) electrophoresis under nonreducing (A) or reducing (B) conditions, blotted to nitrocellulose, and detected with alkaline phosphatase conjugated anti-human IgG. Panel A: lane1=Chimeric L6 mAb (0.5 μg); lane 2=anti-L6 WTD (0.5 μg); lane 3=CD3-L6FvIg bispecific (0.5 μg); lane 4=L6FvIg (0.6 μg); and lane 5=CD3Fv-Ig (0.4 μg). Panel B: lane 1=CD3Fv-Ig (0.4 μg); lane 2=L6FvIg (0.6 μg); lane 3=CD3-L6FvIg bispecific (0.5 μg); lane 4=anti-L6 WTD (0.5 μg); and lane 5=Chimeric L6 mAb (0.5 μg).

The variable region fusion cassettes were inserted into the modified expression vector to create the gene fusions diagrammed in FIG. 2A and transfected into COS cells. Serum free spent medium was collected, and proteins purified by protein A affinity chromatography. Western blots of proteins subjected to reducing or nonreducing SDS-PAGE were probed with alkaline-phosphatase conjugated goat anti-human IgG as shown in FIG. 2B. Panels A and B illustrate that the L6Fv-Ig and CD3Fv-Ig fusion proteins migrated as a single species of $M_r$ 55,000 under both reducing and nonreducing conditions, the approximate size expected for these single chain antibody derivatives. Similarly, the CD3-L6FvIg bispecific molecule migrated as a single species of $M_r$~94,000 under either of these conditions. By comparison, chimeric L6 mAb or L6 wild-type dimer (WTD) consisting of mouse variable regions fused to wild-type sequences for human hinge-CH2–CH3, exhibited significant mobility differences depending on reduction and on the degree of denaturation, indicating that the heavy chain constant regions of these molecules associated by disulfide bonding to form dimers. Occasionally, western blots from nonreducing SDS-PAGE exhibited a very faint band for the monospecific molecules migrating at $M_r$>100,000 or for the bispecific molecule migrating at $M_r$>200,000.

The $V_L$-$V_H$ fusion cassette was inserted into the adapted vector so that a single open reading frame was created including the anti-L6 light chain signal peptide, the variable region fusion encoding the antibody binding specificity, and the human IgG1 Fc domain. The CD3-L6 bispecific fusion cassette was created by fusing the CD3 and L6 fusion cassettes via a short helical peptide linker, and inserted as for the monospecific constructs. The molecular tag utilized in initial tests of the expression system was a mutant derivative of human Fc in which the hinge disulfides were changed to serines to reduce or eliminate intrachain disulfide bonding. These single chain constructs were transfected individually into COS cells and the fusion proteins purified from culture supernatants by affinity chromatography on immobilized protein A.

Yields of purified protein were typically about 2 mg/liter for the L6Ig fusion protein, about 10 mg/liter for CD3Ig, and about 0.5 mg/liter for the CD3-L6Ig bispecific molecule. Western blots of proteins subjected to nonreducing SDS-PAGE and probed with alkaline-phosphatase conjugated goat anti-human IgG are shown in FIG. 2B. A single species is visible in the CD3Ig and L6Ig lanes migrating at Mr 55,000, the approximate size expected for these single chain antibody derivatives, but not in the negative control lane (FIG. 2B). The CD3-L6Ig bispecific molecule migrates at about Mr-95,000–98,000, with a higher molecular weight band visible at Mr>200,000 (FIG. 2B).

Figure 3:
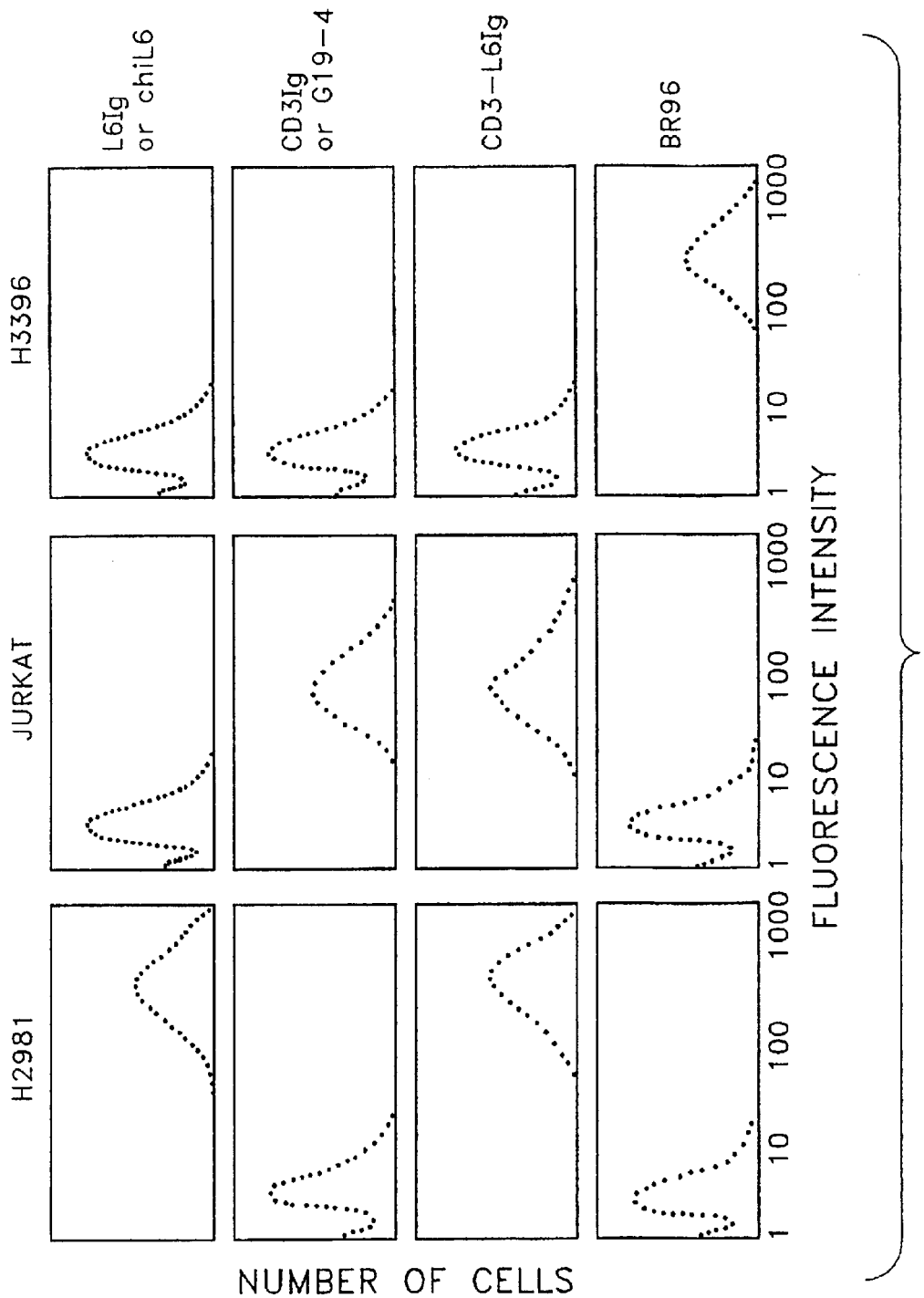
FIG. 3 are FACS plots showing L6FvIg, CD3FvIg, CD3-L6FvIg and BR96 binding to cells expressing target antigen.

Binding activities of L6Ig, CD3Ig, and CD3-L6Ig fusion proteins: To investigate the functional activities of our single chain antibody derivatives and verify that the molecules were capable of antigen specific binding, we first tested binding of the Fc domain fusion proteins to cells expressing target antigen. The human tumor cell line H2981 expresses high levels of L6 target antigen but not CD3 or BR96, while the H3396 human tumor cell line expresses high levels of BR96, but not L6 or CD3, and the human Jurkat cell line expresses CD3, but not L6 or BR96. Binding was detected by fluorescence activated cell sorter analysis using FITC-conjugated goat anti-human Ig as second step reagent. As shown in FIG. 3, the fusion proteins bind specifically to cells expressing target antigen similar to the parent native antibody (i.e., native anti-L6 and G19-4 antibodies), but fail to bind to cells which lack detectable levels of the antigen. The CD3-L6Ig bispecific fusion protein bound to both Jurkat and H2981 cells, an indirect indication that the molecules possess more than one specificity. Similar results were observed whether detection was achieved using goat anti-human IgG or a FITC-conjugated anti-idiotypic antibody directed against the L6 binding specificity.

Antibody derivatives at 10 μg/ml were incubated with H2981 tumor cells (L6 positive), Jurkat cells (CD3 positive), or H3396 tumor cells (BR96 positive) (FIG. 3). The cells were washed and incubated with FITC-conjugated goat anti-human IgG as second step reagent. A total of 10,000 stained cells was then analyzed by FACS (FIG. 3). FIG. 3 shows that L6Ig, CD3Ig, and CD3-L6 Ig bind to cells expressing target antigen.

In order to explore the biological properties of the fusion proteins, we chose different functional assays based on the expected or desired properties of each individual molecule. The results for each single chain molecule will therefore be presented separately beginning with the L6Ig single chain antibody derivatives.

Effects of variations in the molecular tag sequence on the binding activities of L6 fusion proteins: Several different molecular tag sequences were constructed as described in Materials and Methods and fused to the L6 binding domain to determine whether expressed fusion constructs could be detected and purified using these regions as binding targets for protein A or specific antibodies targeted against them. The C-kappa, HIV peptide, and FLAG peptide all failed to function as reliable molecular tags when fused directly to the L6 binding domain. All three of these peptides resulted in a failure of the transfected cells to express recognizable L6. Even when detection did not depend on the molecular tag but utilized the L6 anti-idiotype antibodies, no functional fusion protein was detectable in binding assays to H2981 tumor cells.

Figure 4A:
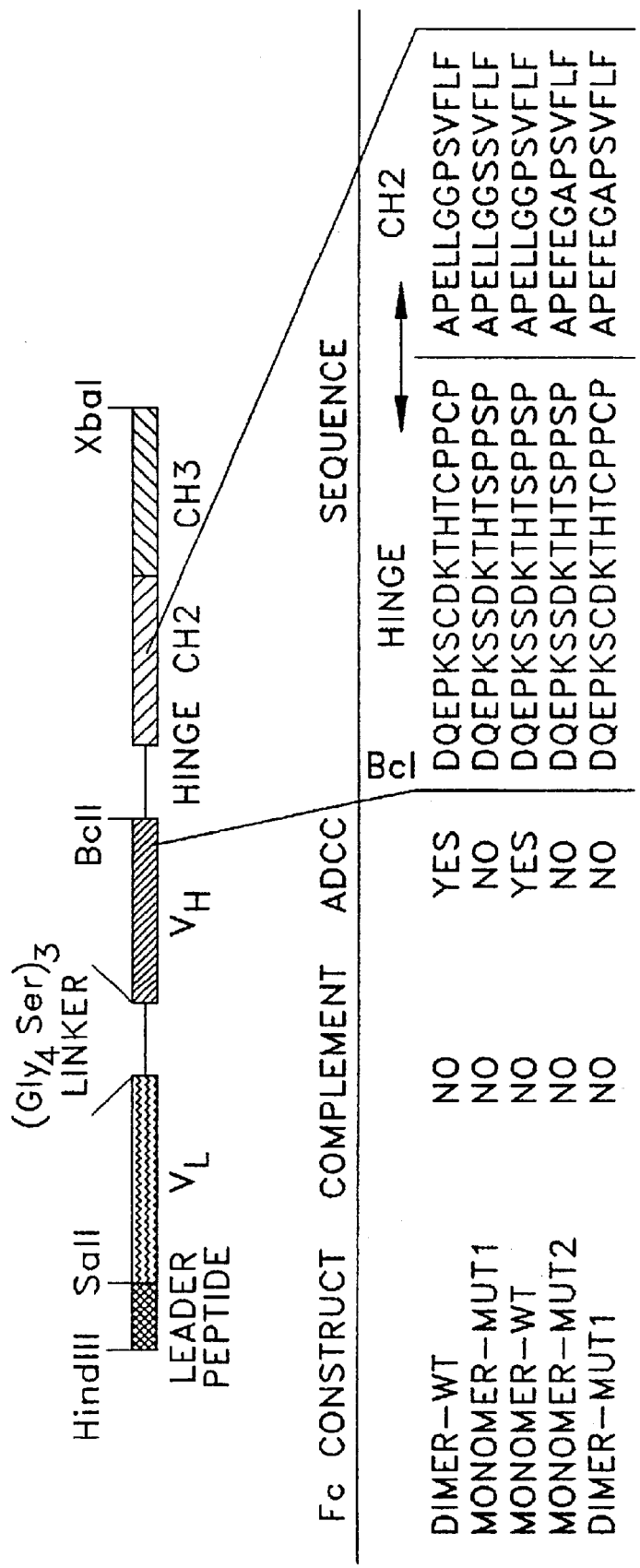
FIG. 4A shows that the L6Fv was fused to several different mutant derivatives of the human IgG1 Fc domain (SEQ ID NO:19, SEQ ID NO:20, SEQ ID NO:21, SEQ ID NO:22, and SEQ ID NO:23). Each mutant and the sequence changes introduced into the hinge and/or the CH2 domain are indicated (SEQ ID NO: 19–23). In addition, the ability of each construct to mediate CDC and ADCC are shown.
Figure 4B:
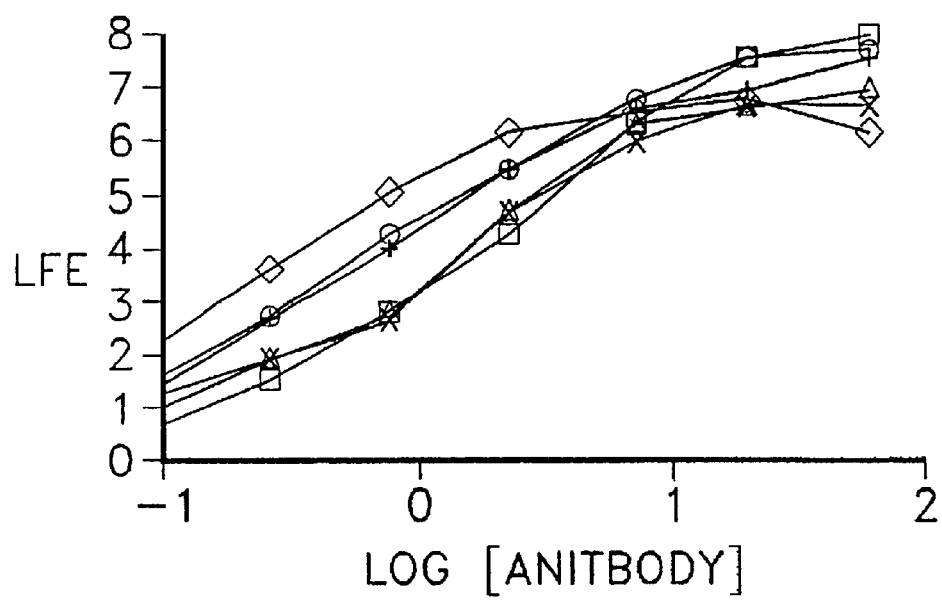
FIG. 4B is a line graph of the saturation analysis of the L6 derivatives or chimeric L6 which were incubated with H2981 tumor cells at progressively lower concentrations (three-fold serial dilutions) and binding was detected with FITC-conjugated anti-idiotype against L6 as second step reagent. Saturation binding curves were generated from these data and fluorescence intensity was plotted as a function of antibody concentration. Legend: Chimeric L6 (open diamond), WTD (open square), DM1 (open triangle), HS1 (plus sign), HS2 ("X" sign), and HS3 (open circle).

Effects of variation in the Fc domain on effector functions by L6 derivatives: Other L6 derivatives were constructed, including a simple sFv of the L6 binding domains with no molecular tag (sFv) and several –Ig fusions attached to different Fc domain mutants. Each Fc construct was given a designation based on the mutations introduced into the hinge and/or the CH2 domain, as illustrated in FIG. 4A and 4B. The wild type dimer (WTD) is wild type for all Fc domain sequences, identical to native antibody for amino acid residues in this region. The monomer constructs contain sequence changes, i.e. cysteine residues, which mutate the hinge disulfides to serines (HS1). Monomer mutant 1 (also known as mut1) (HS2) contains a proline to serine change at residue 238 in the CH2 domain, a region important in mediating IgG1 effector functions. Monomer mut2 (HS3) is mutated for several residues (234–238) in this region of CH2. Dimer mut1 (DM1) contains wildtype sequences in the hinge region of the Fc domain, but is also mutant for CH2 sequences encoding residues 234–238.

Figure 4C:
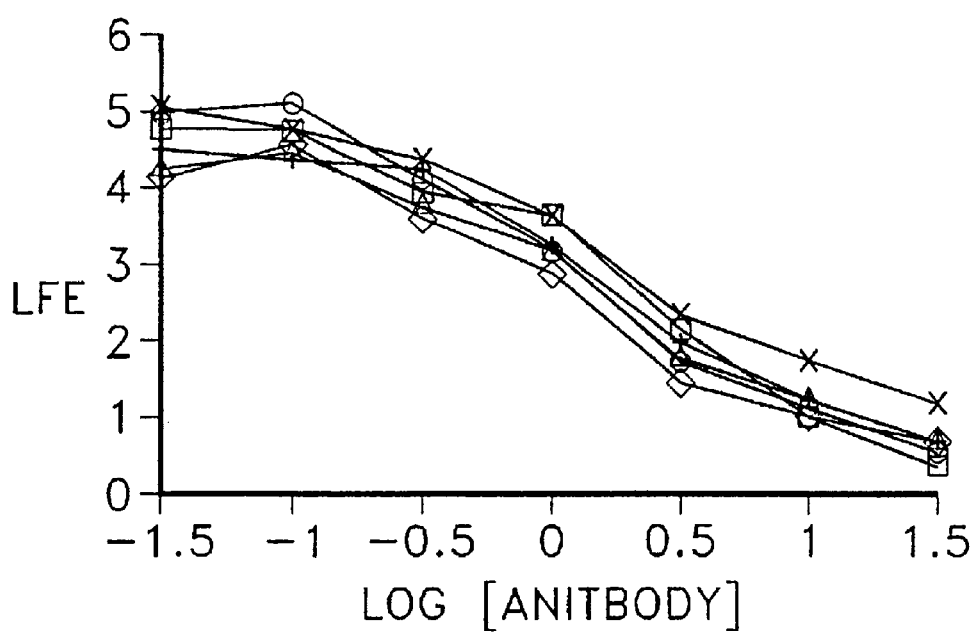
FIG. 4C is a line graph of the inhibition analysis of H2981 tumor cells which were incubated with serial dilutions of each antibody derivative for 30 min and FITC-conjugated L6 at 1 μg/ml for 30 min prior to FACS analysis. The fluorescence intensity was plotted as a function of antibody concentration for each molecule. Legend: Chimeric L6 (open diamond), WTD (open square), DM1 (open triangle), HS1 (plus sign), HS2 ("X" sign), and HS3 (open circle).
Figure 4D:
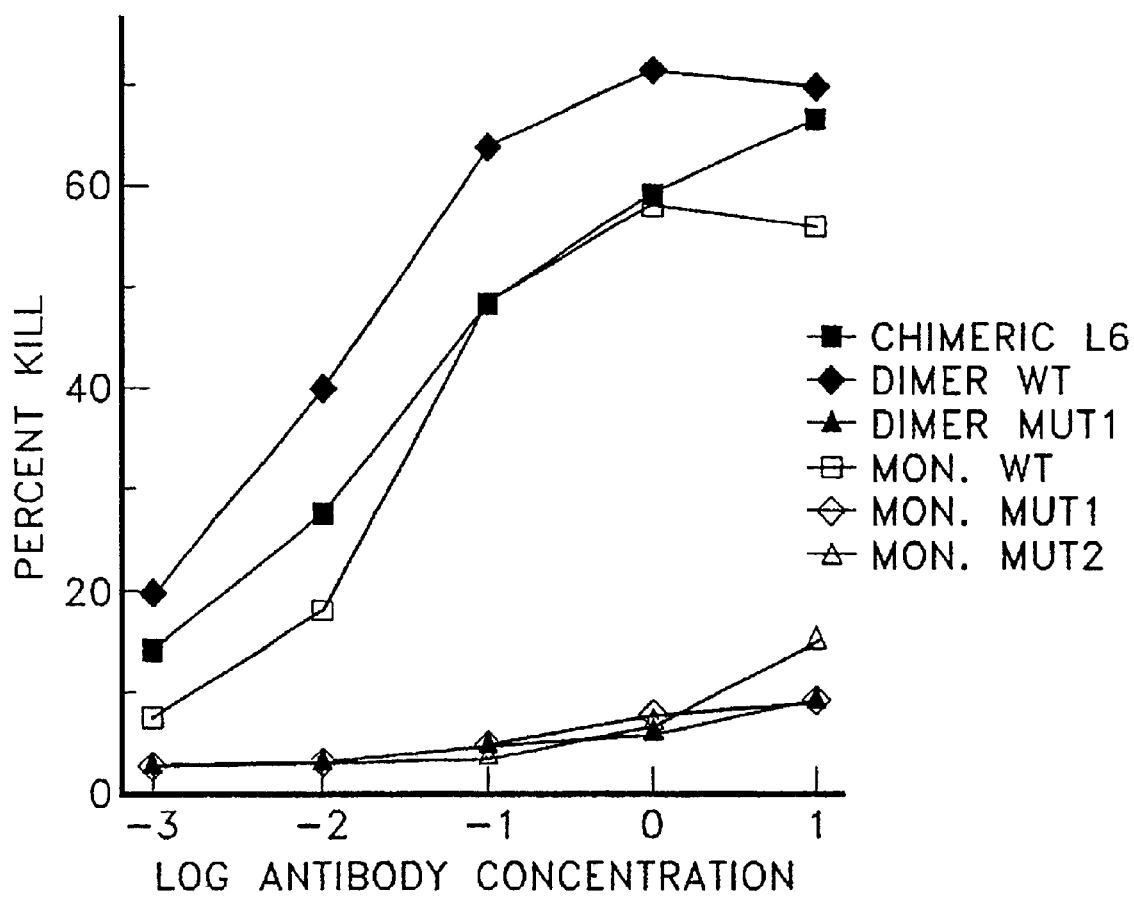
FIG. 4D is a line graph showing the results when H2981 tumor cells were labelled for 2 hours with $^{51}$Cr, washed, and added to IMDM/10% FBS containing 10-fold serial dilutions of antibody derivatives, and human PBL as effector cells at an effector to target ratio of 100:1. Assays were incubated for 4.5 hours, spun, and 100 μl measured for released counts with a gamma counter. Percentage kill was calculated using the following formula: % kill=[(mean cpm-mean spontaneous release)/(mean maximal release-mean spontaneous release)]×100. Values represent the means of triplicate cultures (SEM<10%).

The Sfv for L6 contains a STOP codon after the L6 $V_L$-$V_H$ fusion cassette rather than any other molecular tag peptide sequences. Each of these molecules was constructed, transfected into COS cells, and expressed proteins purified either over protein A sepharose or an immobilized L6 anti-idiotype antibody column. Fusion proteins were compared to native chimeric L6 antibody and Fab' derivatives in saturation and inhibition binding analyses (FIGS. 4C–D). The L6 Fc mutants generated saturation curves very similar to those of native antibody (FIG. 4C), while the Sfv fusion protein bound poorly (FIG. 4B). Inhibition studies were performed by incubating increasing amounts of the test antibody with tumor cells prior to addition of FITC conjugated chimeric L6. Again we observed similar curves for all the –Ig fusions and chimeric antibody (FIG. 4D), with the Sfv and the Fab' exhibiting reduced ability to inhibit binding of native antibody (FIG. 4C). Despite the failure to compete with or inhibit the binding of native antibody, the Sfv fusion protein performed slightly better than the chemically prepared L6 Fab molecule in this experiment.

The relative abilities of these molecules to mediate the effector functions associated with human IgG1 was measured by antibody dependent cellular cytotoxicity (ADCC) or complement dependent cytotoxicity (CDC) assays, and specific lysis plotted as a function of antibody concentration. While none of the mutants defective in the hinge region were affected in their ability to mediate ADCC, all of the CH2 domain mutants failed to mediate this process. Surprisingly, we discovered that although chimeric L6 mediated CDC very well, none of the L6 derivatives were capable of stimulating complement mediated lysis of the tumor targets.

Variable region(s) from the murine antibody directed against the human tumor antigen L6 were fused to several derivatives of the Fc domain from human IgG1 expressed in COS cells, and fusion proteins purified by affinity chromatography (FIGS. 10A–D).

Each Fc domain constructed is indicated with sequence changes indicated by underlined amino acids (FIGS. 10A–D). Purified protein from each construct was compared to chimeric L6 in saturation and inhibition assays. In addition, the ability of these molecules to mediate normal IgG1 effector functions such as ADCC and CDC were measured by labelling H2981 tumor cells for 2 hours with 51 Cr, washing, and adding them to IMDM+10% FCS containing 10-fold serial dilutions of antibody, and either human PBL (ADCC) or rabbit complement (CDC). Assays were incubated for 4.5 hours, spun, and released counts measured with a gamma counter. Values represent the means of triplicate cultures (SEM<10%).

CD3 single chain antibodies exhibit biological activities qualitatively similar to but quantitatively distinct from native antibody: Several different CD3 fusion proteins were constructed, including an –g fusion, an –HIV peptide fusion protein, a $V_L$-$V_H$ sFv (no tag), and the CD3-L6 Fv-Ig bispecific molecule.

The HIV peptide served as a reliable molecular tag when fused to CD3. It permitted detection and purification of CD3 single chain fusion proteins. The tagged molecules were purified by affinity chromatography using immobilized protein A (–Ig fusions) or 110.3 antibody (HIV fusions). The simple Sfv was used as a filtered supernatant solution, and approximate concentrations were estimated by titrating the supernatant's ability to inhibit binding of G19-4 antibody to Jurkat cells. We wished to investigate the cellular responses generated by the binding of these altered molecules to the CD3 T cell receptor complex. Each molecule was bound to indo-1 loaded peripheral blood lymphocytes or T cells and mobilization of intracellular calcium monitored by flow cytometry. As shown in FIGS. 5A–D, transmembrane signalling activity was increased for both the Ig and HIV fusion proteins when compared to equivalent concentrations of native G19-4 antibody. Although the simple Sfv generated a calcium signal, it was not as intense or prolonged as that observed for native antibody.

Figure 11:
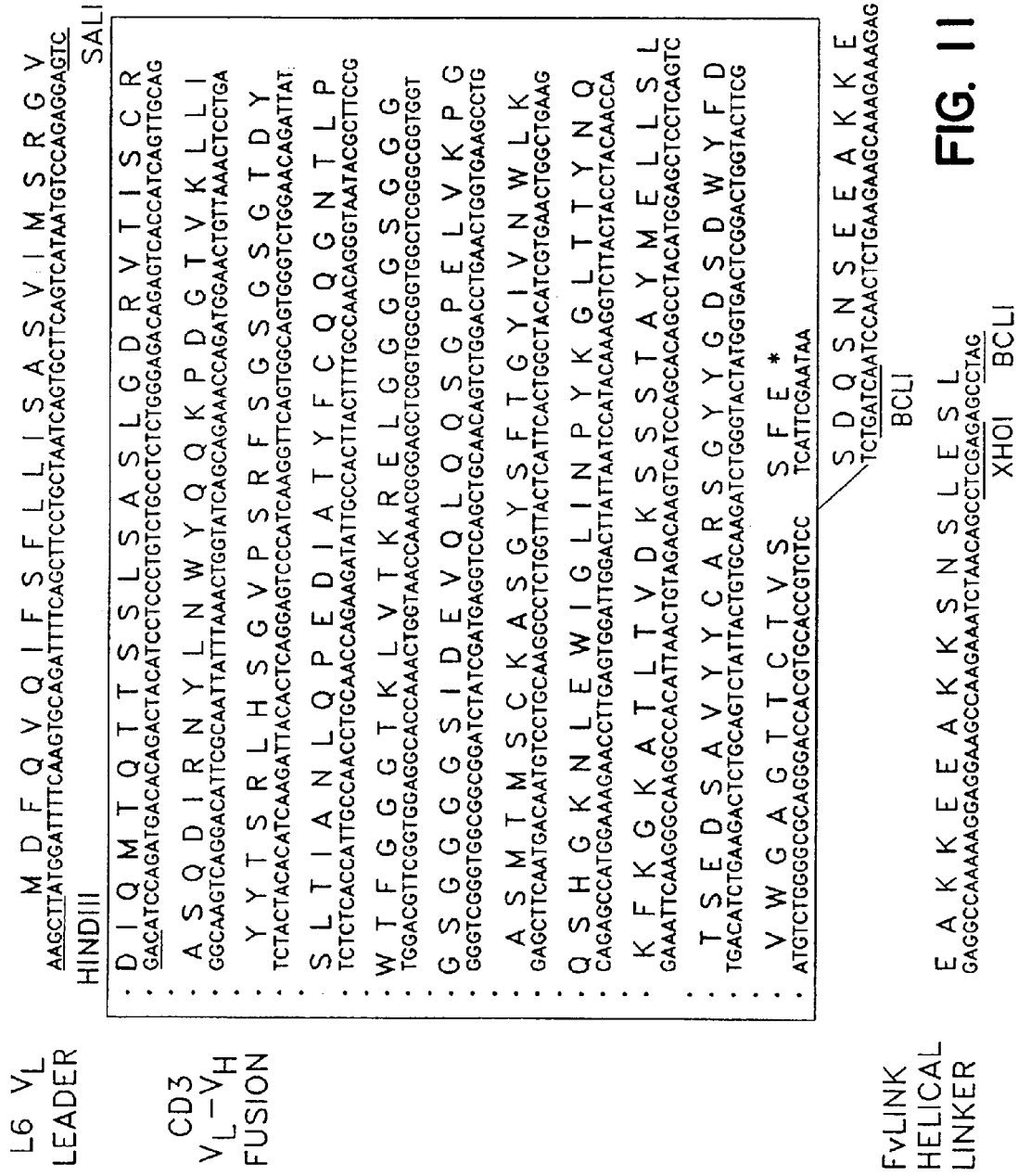
FIG. 11 is the amino acid (SEQ ID NO:32) and nucleic acid sequences (SEQ ID NO:29) of L6V$_L$ leader, CD3 F$_V$ (V$_L$–V$_H$), and the Fvlink helical linker (SEQ ID NO:18).
Figure 12A:
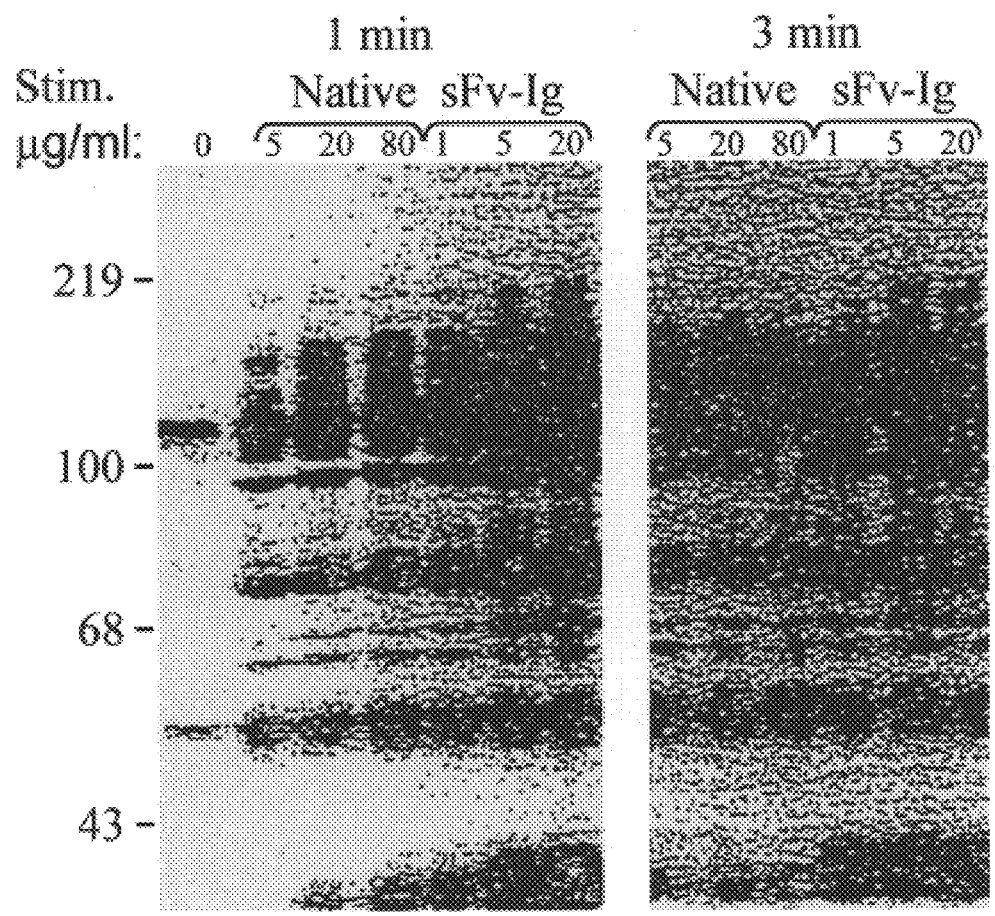
FIGS. 12(A/B) are PAGE gels showing that CD3FVIg stimulates strong tyrosine phosphorylation and activation of PLCγ1 in T cells, and induces the association of PLCγ1 with pp35/36.
Figure 12B:
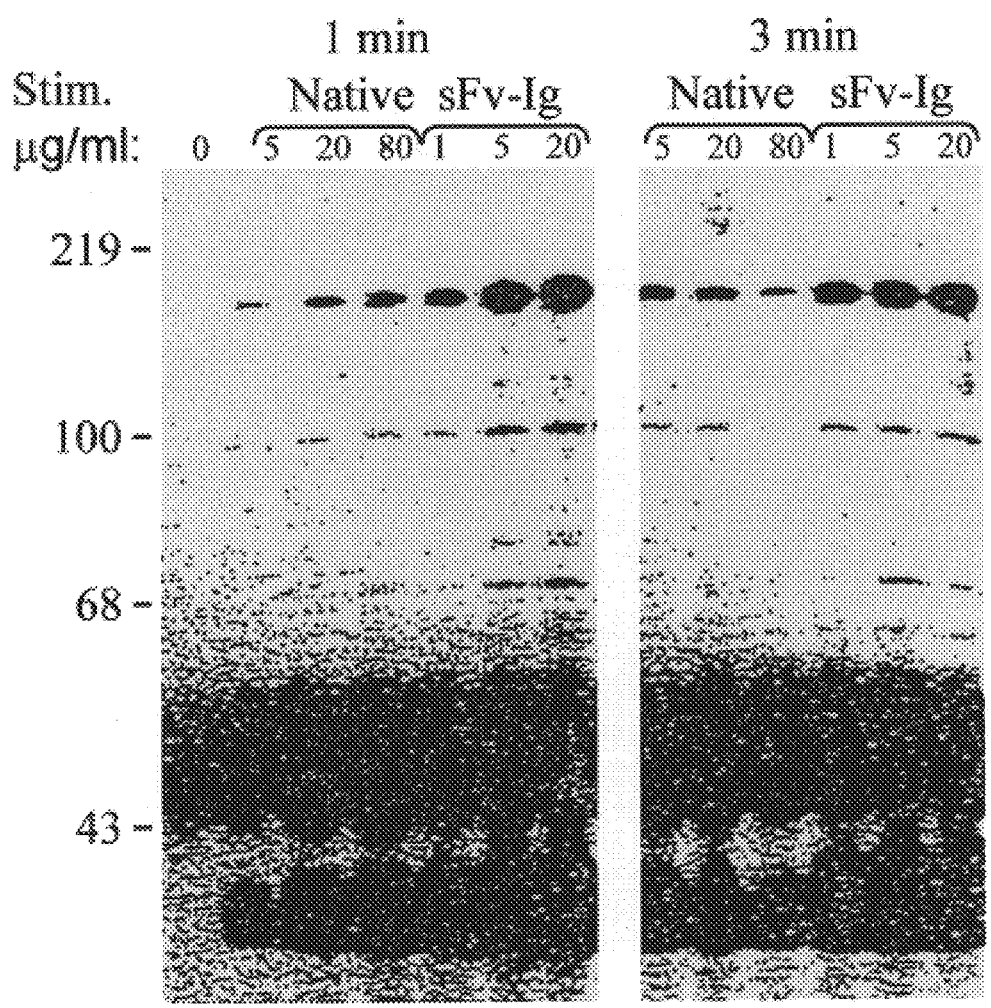

The sequences of the anti-CD3 variable regions are shown in FIG. 11, including the junction sequences for the mono- and bispecific derivatives. The Ig fusion proteins were purified by affinity chromatography using immobilized protein A and the Sfv was used as filtered supernatant. The concentration of Sfv was estimated by titrating the ability of the transfection supernatant to block the binding of known concentrations of parent G19-4 Mab to Jurkat cells. To analyze the signaling activity of the CD3Fv-Ig molecule, it was tested for its ability to induce tyrosine phosphorylation of PLCγ1. Jurkat T cells were stimulated with the CD3Fv-Ig or native G19-4 Mab and proteins from the cell lysates were separated by SDS-PAGE, transferred to PDVF membrane, and probed with either anti-p-tyr or anti-PLCγ1. Surprisingly, we found that the CD3FV-Ig induced strong tyrosine phosphorylation of cellular proteins in whole cell lysates including PLCγ1 and that a greater amount of pp35/36 phosphoprotein was associating with PLCγ1 (FIGS. 12A–B). Moreover, both the CD3 Fv-Ig and the CD3 Sfv proteins induced calcium fluxes in PBL that were greater in magnitude than those observed for equivalent concentrations of native G19-4 Mab.

In FIG. 11, the variable regions from the heavy and light chains of anti-CD3 Mab G19-4 were cloned by PCR. The nucleotide and protein sequence of the gene fusion constructed from these CDNA cassettes is shown with the $(Gly_4Ser)_3$ linker in bold typeface. The amino terminus of the $V_L$–$V_H$ fusion cassette was fused at the SalI site to the L6 light chain variable region leader peptide, and the carboxy terminus was fused directly to the hinge region of the Fc domain at the BclI site or to a short "helical" peptide linker to construct the bispecific CD3-L6FvIg antibody derivative. The variable regions for L6 were fused in frame to the opposite end of the "helical" linker as shown in FIGS. 1 and 2.

In FIGS. 12A–B Jurkat cells ($10^7$ per sample) were stimulated for 1 minute (min) or 3 min with native anti-CD3 Mab G19-4 at 5,20 or 80 μg/ml or with CD3Fv-Ig at 1, 5, or 20 μg/ml, as indicated. Proteins from cell lysates were immunoprecipitated with rabbit anti-p-tyr (Panel A) or PLCγ1 antiserum (Panel B) and were recovered with protein A sepharose, separated by SDS-PAGE, transferred to nitrocellulose and detected with purified rabbit anti-p-tyr and $^{125}$I-labelled protein A.

Figure 5A:
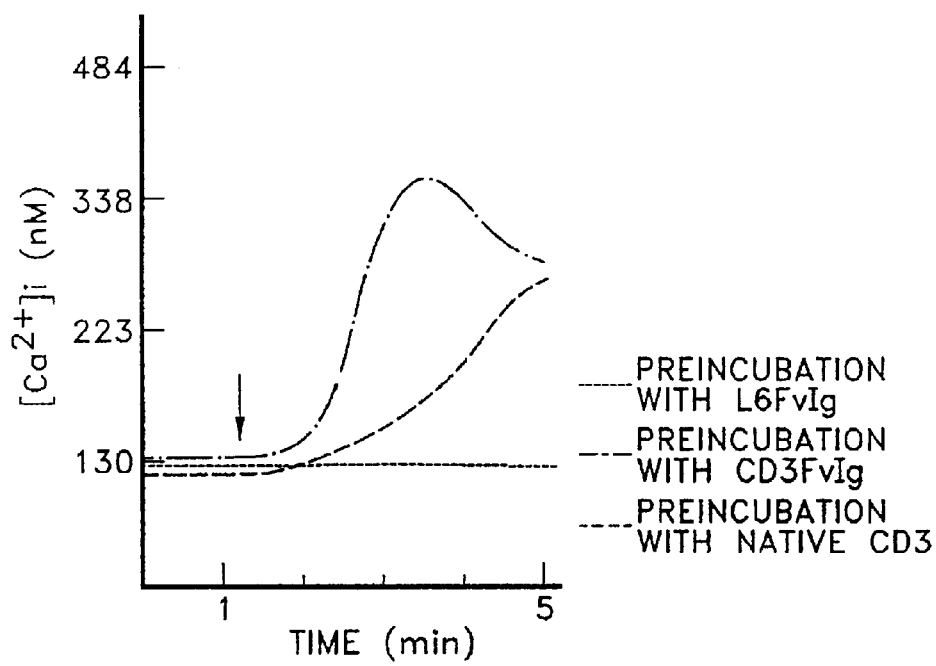
FIGS. 5A–D are line graphs showing that CD3FvIg mobilizes intracellular calcium in peripheral blood T cells and that pretreatment with CD3FvIg desensitizes the response of peripheral blood T cells to subsequent simulation of cross linked CD2.
Figure 5B:
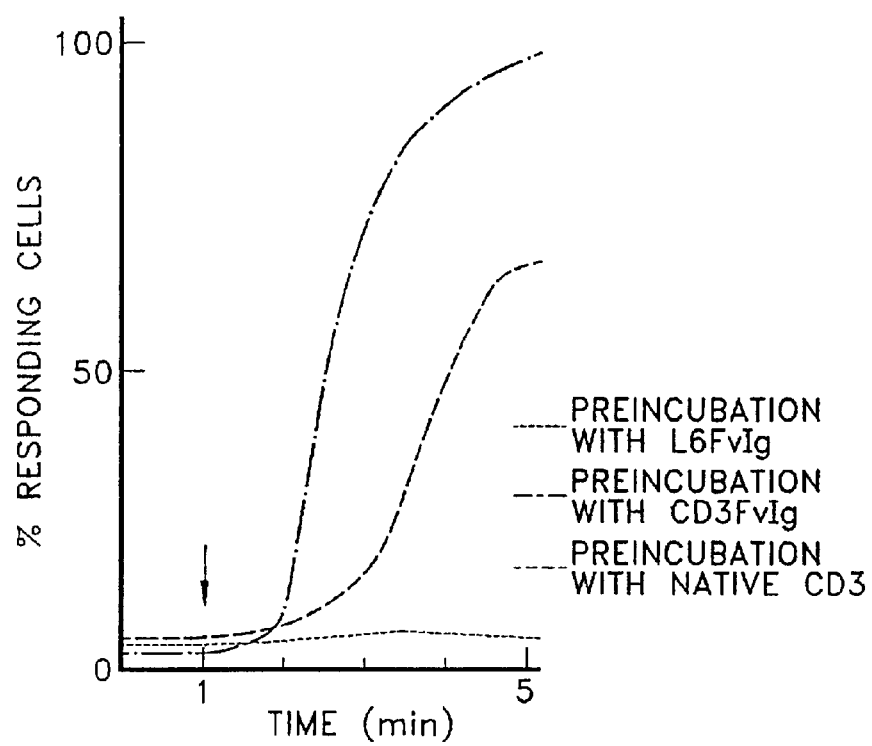

FIGS. 5A–D are line graphs showing that CD3Fv fusion derivatives exhibit different levels of transmembrane signalling activity. FIGS. 5A–B show that CD3FvIg mobilizes intracellular calcium in peripheral blood T cells. Flow cytometry and the calcium binding dye indo-1 were used to monitor the concentration of intracellular free calcium ($[Ca^{2+}]$) following stimulation with CD3FvIg (_._._), native CD3 Mab (- - - -), or a non T cell binding control-L6FvIg( . . . . ). Each stimulus (2 μg) was added to indo-1 loaded T cells at 1 min (arrow) where 130 nm=resting cells, and as percent responding cells.

Figure 5C:
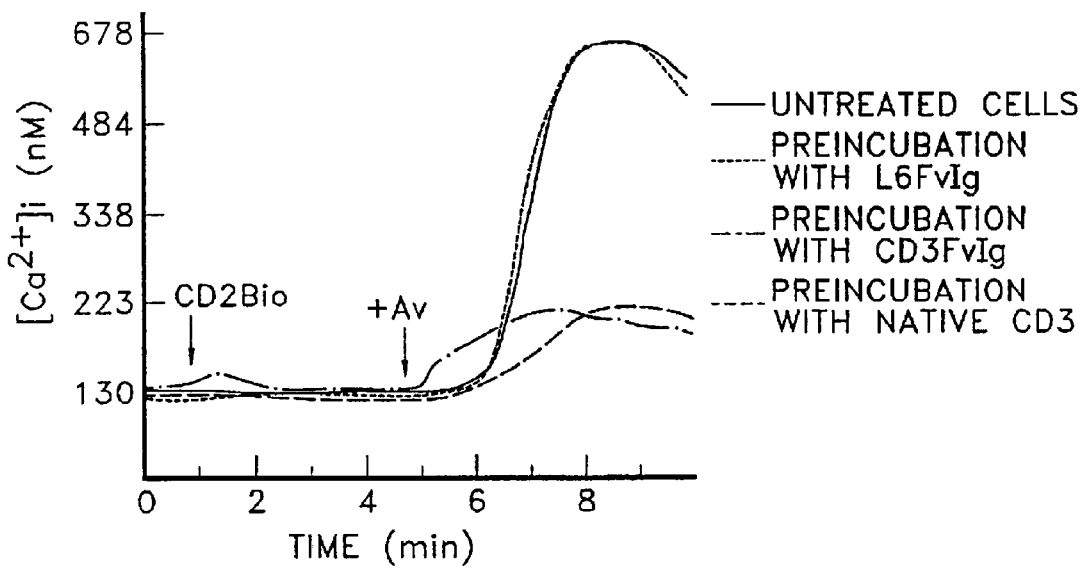
Figure 5D:
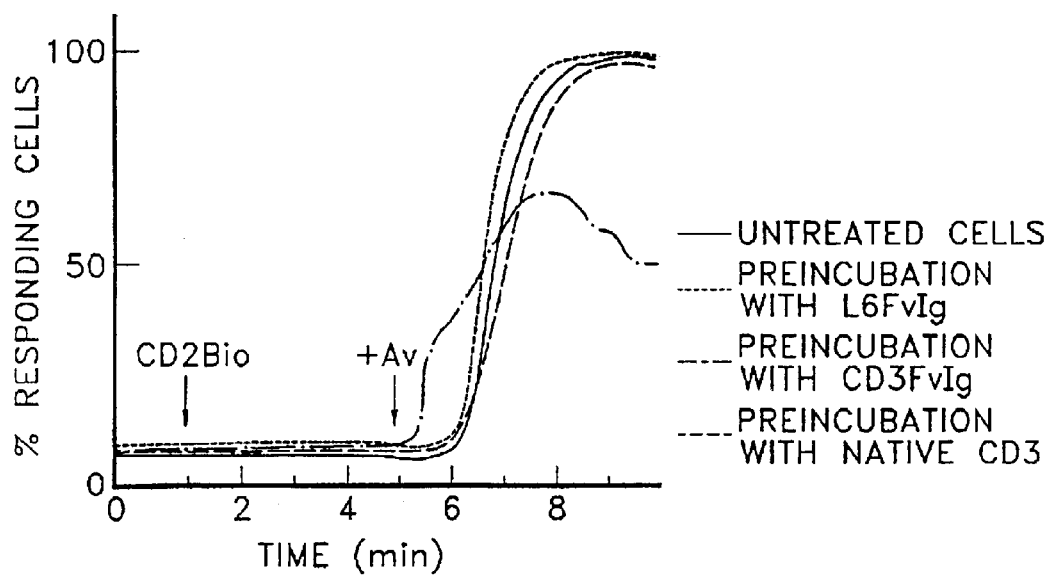

FIGS. 5C–D shows the pretreatment with CD3FvIg desensitizes the response of peripheral blood T cells to subsequent stimulation of cross linked CD2. Indo-1 loaded cells were incubated with 1 μg of CD3FvIg, 2 μg of native CD3 mAb, or L6FvIg (non T cell binding control) for 15 minutes at 37 degrees centigrade. Biotinylated anti-CD2 mAb (5 μg) was added at 1 min and was cross linked by avidin (20 μg) at 5 min. Responses to cross linked CD2 were then monitored for 5 min. Data are represented as ($[Ca^{2+}]$) where 130 nM=resting cells (panel A), and as percent responding cells (panel B).

In proliferation assays of peripheral blood lymphocytes and purified T cells responding to stimulation with the CD3 antibody derivatives at various concentrations, we found that all the CD3 derivatives activated T cells. In Table 1, the proliferative responses measured at antibody treatments of 1 μg/ml are shown. A similar pattern of proliferative responses was observed at both 0.2 and 5 μg/ml. The data indicate that binding of the CD3 derivatives elicits proliferative responses in T cells similar to those observed with either native G19-4 (compared to the CD3Fv-Ig) or the Fab fragment (compared to the sFv) of the murine antibody. The genetically engineered molecules stimulated slightly stronger levels of proliferation from purified T cells, and slightly weaker levels from PBL, with the exception of CD3Fv-Ig acting in synergy with PMA to produce stronger proliferative responses in PBL than those observed with native G19-4.

Because the two tagged CD3 fusion proteins exhibited stronger transmembrane signalling activity than native antibody, we wished to determine how these molecules affected T cell proliferation. Peripheral blood lymphocytes and purified T cells were incubated for 72 hours with antibody derivatives at various concentrations and pulsed with tritiated thymidine for 6 hours prior to harvesting and counting. Table 1 displays results of antibody treatments at 1 μg/ml. A similar pattern of proliferative responses was observed at both 0.2 and 5 μg/ml as well.

TABLE 1

CD3 Single Chain Molecules Stimulate T Cell Proliferation in the Presence of Monocytes and are Synergistic for Activation of T Cells in the Presence of PMA or 9.3.

| | Proliferation (day 3, cpm × $10^{-3}$) | | |
|---|---|---|---|
| Stimulus | Purified T Cells + (2 μg/ml 9.3) | PBMC + Medium | Purified T Cells + (0.5 ng/ml PMA) |
| Medium | 0.8 | 2.7 | 6 |
| G19-4 | 11.2 | 49 | 83.6 |
| CD3FvIg | 9.3 | 55.6 | 112.5 |
| CD3HIV | 105 | 30.5 | 103 |
| G19-4 Fab | 58.4 | 2.1 | N.D. |
| OKT3 | 6.15 | 77 | 76 |
| BC3 | 2.95 | 0.8 | 87.3 |
| CD3STOP (25 ul) | 55 | 3.4 | 65 |
| L6FvIg | 0.5 | 2.6 | 5.7 |

Proliferation was measured after 72 hours of culture by pulsing cells for 6 hours with 1 μCi/well[$^3$H]-thymidine. T cells were purified away from monocytes and B cells by two plastic adherence followed by passage over nylon wool columns.

The data indicate that under the conditions examined here, binding of the CD3 derivatives elicits proliferative responses in T cells similar to those observed with either G19-4 (Ig fusion) or the Fab fragment (HIV and STOP fusions) of the murine antibody. The genetically engineered molecules tended to stimulate slightly stronger levels of proliferation from purified T cells, and slightly weaker levels from PBL, although the differences are insignificant in most instances. The only exception to this pattern is the stronger proliferative response generated by the CD3sFvIg and CD3HIV constructs in synergy with PMA when compared with native G19-4.

CD3-L6 Bispecific Fusion Protein Mediates Adhesion Between Jurkat and H2981 Tumor Cells. A previously developed cell adhesion assay (Linsley et al., 1990a) was used to determine whether a single CD3-L6 bispecific molecule was capable of binding to CD3- or L6- expressing cells simultaneously.

Jurkat cells were first incubated with anti-CD3 or with CD3-L6FvIg. Cells were washed and added to adherent H2981 cells preincubated with or without L6FvIg. Microscopic examination of the H2981 monolayers (FIG. 6) demonstrated that CD3-L6FvIg protein mediated adhesion between Jurkat and H2981 cells in the presence of EDTA, but only when CD3 and L6 receptors were not blocked by ligand. To demonstrate quantitatively that the molecules were truly bifunctional, Jurkat cells were prelabelled with $^{51}$Cr and then incubated with the fusion protein and H2981 tumor cells. The number of counts bound to the unlabelled monolayer in the presence of the CD3-L6 bispecific fusion protein was much higher than for cells prebound to the unlinked CD3 and L6 antibodies.

Figure 7:
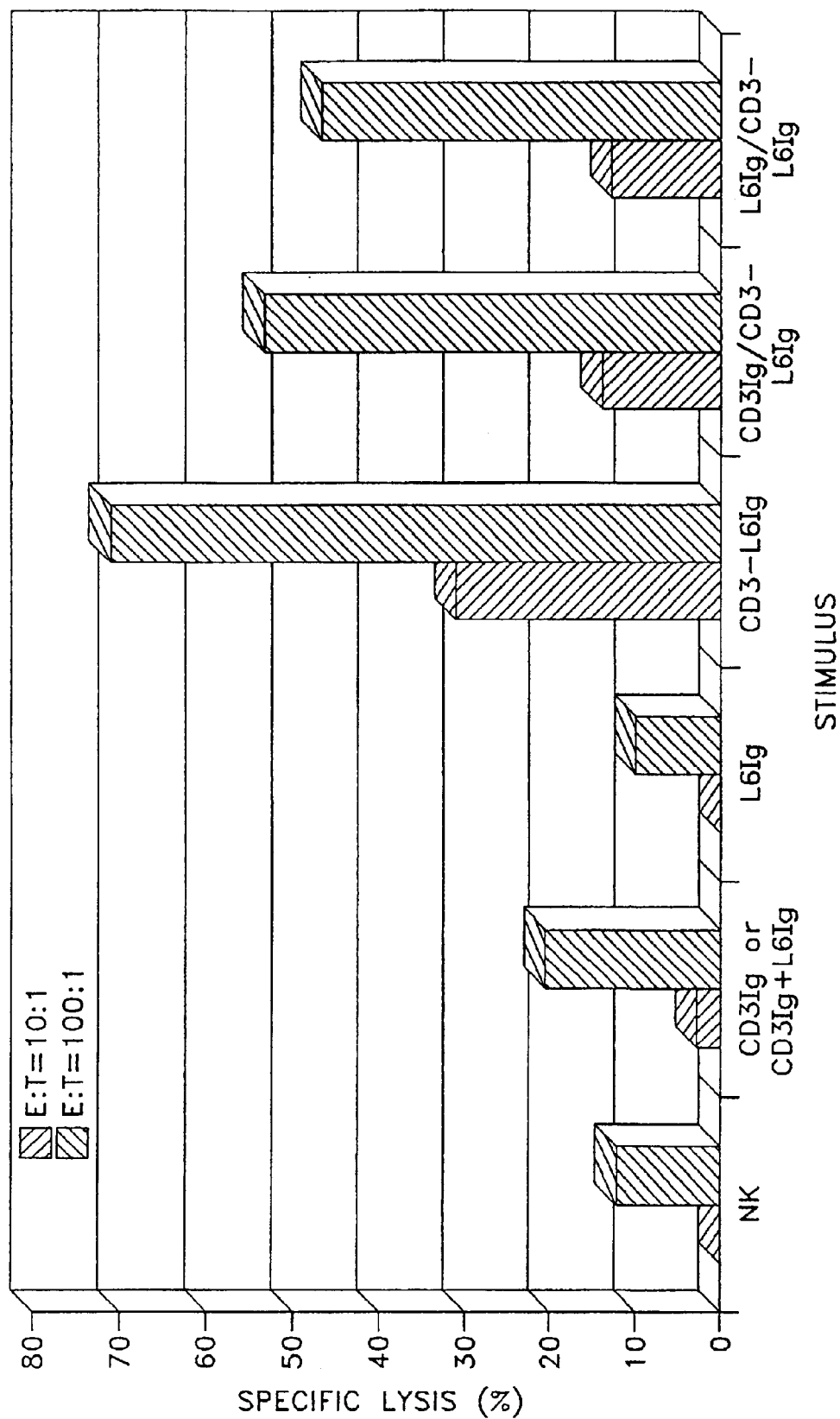
FIG. 7 is a bar graph showing that CD3-L6FvIg bispecific fusion proteins target T cell cytotoxicity to H2981 tumor cells.

CD3-L6Ig bispecific fusion protein targets T cell cytotoxicity to H2981 tumor cells (FIG. 7). H2981 tumor cells were labelled for 2 hours with $^{51}$Cr and incubated with antibody stimuli and PBL at effector to target ratios of 10:1 and 100:1 (FIG. 7). Chromium release was measured as described in Materials and Methods, and specific lysis tabulated for each antibody derivative from triplicate cultures (SEM<12%) (FIG. 7). For inhibition assays, the CD3 or L6Ig monospecific derivatives were incubated with the appropriate cell type prior to addition of the CD3-L6Ig bispecific molecule (FIG. 7). Preincubation with either monospecific molecules was unable to inhibit stimulation of cytotoxicity by the bispecific construct (FIG. 7).

CD3-L6 Bispecific Fusion Protein Targets T Cell Cytotoxicity to H2981 Tumor Cells. Next, we wished to determine the biological consequences of coupling these two antigen binding domains into a single molecule. We reasoned that genetically engineered bifunctional molecules which promote adhesion between tumor cells and T cells might alter the nature or magnitude of responses to receptor binding.

To eliminate background contributions from IgG-mediated effector functions, the antigen binding portion of the molecule was attached to the Fc monomer mutant which fails to mediate these functions as a result of a proline to serine mutation in CH2 and several cysteine to serine substitutions in the hinge region. A standard cytotoxicity assay using H2981 tumor cells as the targets for lysis was performed. Resting PBL were used as effector cells to determine if resting or native cells could be activated to target their cytotoxicity to the tumor (FIG. 7).

At effector to target ratios of 10:1, the CD3-L6FvIg molecule mediated 30% specific lysis, while at ratios of 100:1, specific lysis rose to 71%. The level of specific lysis for CD3FvIg and L6FvIg mixed together, or for either molecule alone ranged from 3% to 5% at E:T of 10:1, and 9% to 20% at E:T of 100:1. Although kill levels were reduced slightly, the CD3FvIg and L6FvIg antibody derivatives failed to completely block the targeted cytotoxicity mediated by the CD3-L6 fusion protein. PHA activated T cell blasts were also used as effectors in this assay, but exhibited high levels of background killing.

Figure 8:
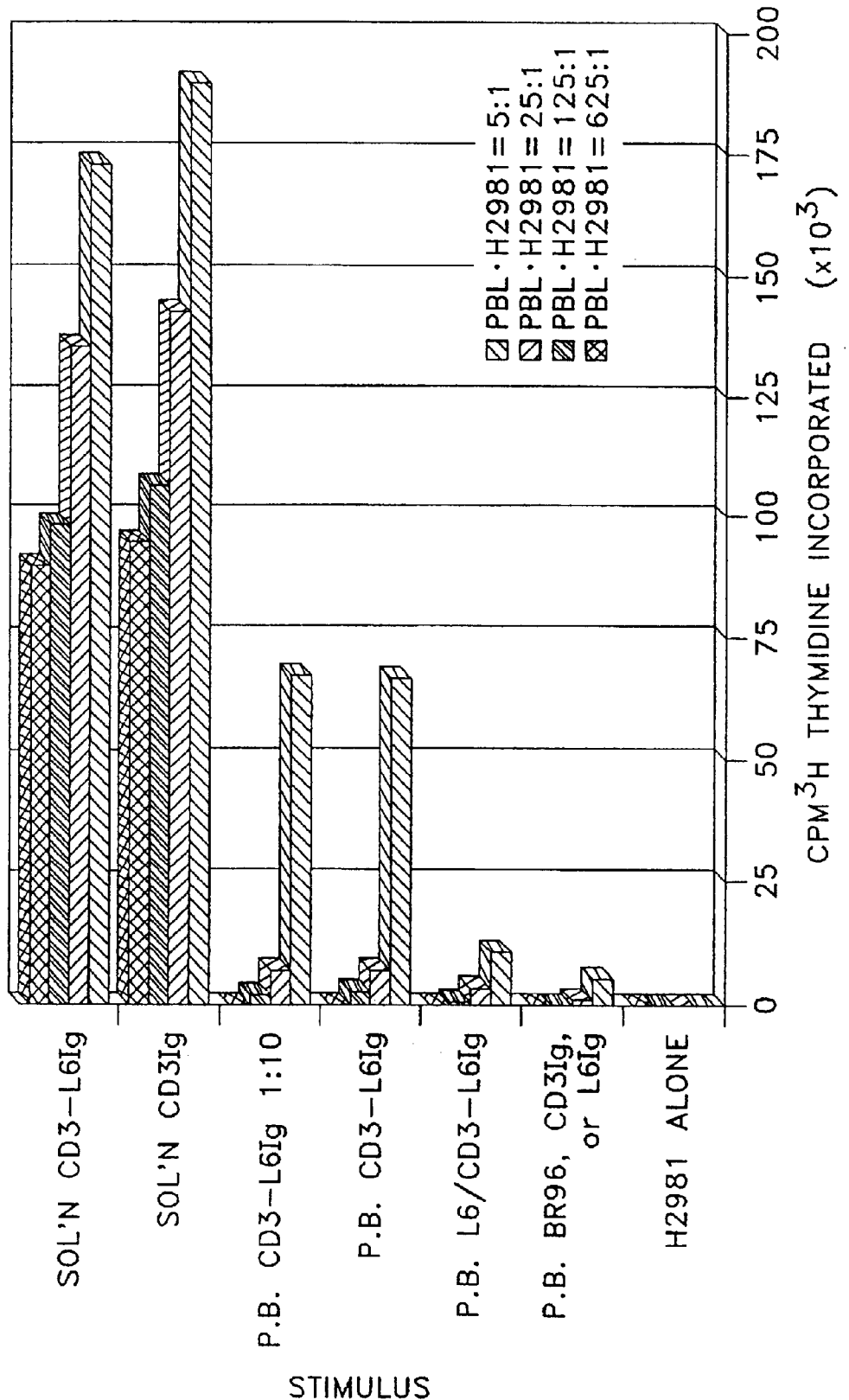
FIG. 8 is a bar graph showing that CD3-L6FvIg bispecific protein stimulates high levels of T cell proliferation when bound to H2981 Tumor Cells.

CD3-L6Ig bispecific fusion protein stimulates high levels of T cell proliferation when bound to H2981 tumor cells (FIG. 8). PBL were isolated and cultured in the presence of the indicated stimulators of T cell proliferation and irradiated H2981 tumor cells. Stimulators were added in solution at either 1 or 10 μg/ml. For prebinding experiments, H2981 tumor cells were irradiated and incubated with 10 μg/ml antibody derivative for one hour on ice, washed several times to remove unbound antibody, and added at varying ratios to PBL at $5\times10^4$ cell/well. After three days of culture, proliferation was measured by uptake of [$^3$H]thymidine for 6 hours. Values were determined by quadruplicate cultures for each treatment (SEM<15%).

CD3-L6 Bispecific Fusion Protein Stimulates High Levels of T Cell Proliferation In Vitro. We investigated whether triggering the CD3 T cell surface receptor (CD3/TCR complex) by the CD3-L6FvIg fusion protein was stimulatory for T cell proliferation. Proliferation assays were performed using resting PBL incubated with irradiated H2981 tumor cells and the stimuli (fusion protein) in solution.

Alternatively, stimulating proteins were prebound to the irradiated tumor cells and unbound protein was removed by several washes prior to inclusion in the assay, eliminating molecules incapable of binding to L6 antigen from contribution to stimulation of T cells through CD3. The H2981 tumor cells tended to bind nonspecifically even to those antibody derivatives mutated in the Fc domain, so to eliminate this source of nonspecific background from the assay, an irrelevant antibody was incubated with the cells before addition of the stimuli of interest. FIG. 8 displays the results of both the solution and prebinding proliferation experiments.

The levels of proliferation were markedly enhanced in the presence of the CD3-L6FvIg bispecific fusion protein at 10 μg/ml, and significant levels of proliferation were observed even at 1 μg/ml. Prebinding L6FvIg to the tumor cells before addition of the bispecific molecule eliminated this stimulation of T cell proliferation induced by the coated tumor cells. CD3IG fusion protein could stimulate significant levels of proliferation when present in solution independent of the presence or absence of the tumor cells. These molecules were evidently removed in the washing steps of the tumor cell prebinding assays because only background levels of proliferation were observed under these conditions. These results demonstrate the ability of the CD3-L6 bispecific fusion protein to target T cell cytotoxicity and stimulated T cell proliferation when bound to H2981 tumor cells.

What is claimed is:

1. A fusion protein that mediates antibody dependent cellular cytotoxicity comprising an extracellular domain of CTLA4 molecule that binds a B7 antigen and a portion of a modified immunoglobulin molecule which mediates antibody dependent cellular cytoxicity, wherein the modified immunoglobulin molecule has a CH2 domain comprising amino acids 18–30 of SEQ ID NO:21, wherein leucine at position 21 is replaced with phenylalanine.

2. A fusion protein that mediates antibody dependent cellular cytotoxicity comprising an extracellular domain of CTLA4 molecule that binds a B7 antigen and a portion of a modified immunoglobulin molecule which mediates antibody dependent cellular cytoxicity, wherein the modified immunoglobulin molecule has a CH2 domain comprising amino acids 18–30 of SEQ ID NO:21, wherein leucine at position 22 is replaced with glutamate.

3. A fusion protein that mediates antibody dependent cellular cytotoxicity comprising an extracellular domain of CTLA4 molecule that binds a B7 antigen and a portion of a modified immunoglobulin molecule, wherein the modified immunoglobulin molecule has a CH2 domain comprising amino acids 18–30 of SEQ ID NO:21, wherein glycine at position 24 is replaced with alanine.

4. A fusion protein that mediates antibody dependent cellular cytotoxicity comprising an extracellular domain of CTLA4 molecule that binds a B7 antigen and a portion of a modified immunoglobulin molecule, wherein the modified immunoglobulin molecule has a CH2 domain comprising amino acids 18–30 of SEQ ID NO:21, wherein proline at position 25 is replaced with serine.

5. A fusion protein that mediates antibody dependent cellular cytoxicity comprising an extracellular domain of CTLA4 molecule that binds a B7 antigen and a portion of a modified immunoglobulin molecule which mediates antibody dependent cellular cytoxicity, wherein the modified immunoglobulin molecule has a CH2 domain comprising amino acids:

a. 18–30 of SEQ ID NO:20, b. 18–30 of SEQ ID NO:22, or c. 18–30 of SEQ ID NO:23.

6. A fusion protein that mediates antibody dependent cellular cytotoxicity comprising an extracellular domain of CTLA4 molecule that binds a B7 antigen and a portion of a modified immunoglobulin molecule, wherein the modified immunoglobulin molecule has a hinge and CH2 domains comprising amino acids:

a. 3–30 of SEQ ID NO:20,
b. 3–30 of SEQ ID NO:22, or
c. 3–30 of SEQ ID NO:23.

* * * * *

SEQUENCE LISTING

```
<160> NUMBER OF SEQ ID NOS: 32

<210> SEQ ID NO 1
<211> LENGTH: 72
<212> TYPE: DNA
<213> ORGANISM: Homo sapiens

<400> SEQUENCE: 1
agcttatgga ttttcaagtg cagattttca gcttcctgct aatcagtgct tcagtcataa    60
tgtccagagg ag                                                        72

<210> SEQ ID NO 2
<211> LENGTH: 72
<212> TYPE: DNA
<213> ORGANISM: Homo sapiens

<400> SEQUENCE: 2
```

```
tcgactcctc tggacattat gactgaagca ctgattagca ggaagctgaa aatctgcact      60
tgaaaatcca ta                                                          72

<210> SEQ ID NO 3
<211> LENGTH: 20
<212> TYPE: PRT
<213> ORGANISM: Homo sapiens

<400> SEQUENCE: 3

Arg Lys Ser Ile Arg Ile Gln Arg Gly Pro Gly Arg Ala Phe Val Thr
 1               5                  10                  15

Ile Gly Lys Ile
            20

<210> SEQ ID NO 4
<211> LENGTH: 76
<212> TYPE: DNA
<213> ORGANISM: Homo sapiens

<400> SEQUENCE: 4
gatcaagatc cgcggaaatc gattagaatc cagagaggcc ctgggcgcgc cttcgttacg      60
atcggcaaga tctagt                                                      76

<210> SEQ ID NO 5
<211> LENGTH: 76
<212> TYPE: DNA
<213> ORGANISM: Homo sapiens

<400> SEQUENCE: 5
ctagactaga tcttgccgat cgtaacgaag gcgcgcccag ggcctctctg gattctaatc      60
gatttccgcg gatctt                                                      76

<210> SEQ ID NO 6
<211> LENGTH: 51
<212> TYPE: DNA
<213> ORGANISM: Homo sapiens

<400> SEQUENCE: 6
gatcaagact acaaggacga cgatgacaag tgagcggccg cgaattcgtc t               51

<210> SEQ ID NO 7
<211> LENGTH: 51
<212> TYPE: DNA
<213> ORGANISM: Homo sapiens

<400> SEQUENCE: 7
ctagagacga attcgcggcc gctcacttgt catcgtcgtc cttgtagtct t               51

<210> SEQ ID NO 8
<211> LENGTH: 39
<212> TYPE: DNA
<213> ORGANISM: Homo sapiens

<400> SEQUENCE: 8
ggtgctctga tcactgtggc tgcaccatct gtcttcatc                             39

<210> SEQ ID NO 9
<211> LENGTH: 39
<212> TYPE: DNA
<213> ORGANISM: Homo sapiens

<400> SEQUENCE: 9
```

```
cctcctcatt ctagactaac actctcccct gttgaagct                                    39

<210> SEQ ID NO 10
<211> LENGTH: 77
<212> TYPE: DNA
<213> ORGANISM: Homo sapiens

<400> SEQUENCE: 10
gatcaatcca actctgaaga agcaaagaaa gaggaggcca aaaggagga agccaagaat              60 ctaacagcct cgagagc                                                            77

<210> SEQ ID NO 11
<211> LENGTH: 78
<212> TYPE: DNA
<213> ORGANISM: Homo sapiens

<400> SEQUENCE: 11
gatcgctctc gaggctgtta gatttcttgg cttcctcctt tttggcctcc tctttctttg             60
cttcttcaga gttggatt                                                           78

<210> SEQ ID NO 12
<211> LENGTH: 27
<212> TYPE: PRT
<213> ORGANISM: Homo sapiens

<400> SEQUENCE: 12

Asp Gln Ser Asn Ser Glu Glu Ala Lys Lys Glu Glu Ala Lys Lys Glu
 1               5                  10                  15

Glu Ala Lys Lys Ser Asn Ser Leu Glu Ser Leu
                20                  25

<210> SEQ ID NO 13
<211> LENGTH: 35
<212> TYPE: DNA
<213> ORGANISM: Homo sapiens

<400> SEQUENCE: 13
gcatgtgcaa gtccgatgag tcccccccccc ccccc                                       35

<210> SEQ ID NO 14
<211> LENGTH: 36
<212> TYPE: DNA
<213> ORGANISM: Homo sapiens

<400> SEQUENCE: 14
acgtcgagaa ttcgcatgtg caagtccgat gagtcc                                       36

<210> SEQ ID NO 15
<211> LENGTH: 30
<212> TYPE: DNA
<213> ORGANISM: Homo sapiens

<400> SEQUENCE: 15
atctccacac acaggaacca gtggatagac                                              30

<210> SEQ ID NO 16
<211> LENGTH: 25
<212> TYPE: DNA
<213> ORGANISM: Homo sapiens

<400> SEQUENCE: 16
```

```
cttccacttg acattgatgt ctttg                                              25
```

<210> SEQ ID NO 17
<211> LENGTH: 22
<212> TYPE: DNA
<213> ORGANISM: Homo sapiens

<400> SEQUENCE: 17

```
caagaagcac acgactgagg ca                                                 22
```

<210> SEQ ID NO 18
<211> LENGTH: 302
<212> TYPE: PRT
<213> ORGANISM: Homo sapiens

<400> SEQUENCE: 18

```
Met Asp Phe Gln Val Gln Ile Phe Ser Phe Leu Leu Ile Ser Ala Ser
  1               5                  10                  15

Val Ile Met Ser Arg Gly Val Asp Ile Gln Met Thr Gln Thr Thr Ser
                 20                  25                  30

Ser Leu Ser Ala Ser Leu Gly Asp Arg Val Thr Ile Ser Cys Arg Ala
             35                  40                  45

Ser Gln Asp Ile Arg Asn Tyr Leu Asn Trp Tyr Gln Gln Lys Pro Asp
         50                  55                  60

Gly Thr Val Lys Leu Leu Ile Tyr Tyr Thr Ser Arg Leu His Ser Gly
 65                  70                  75                  80

Val Pro Ser Arg Phe Ser Gly Ser Gly Ser Gly Thr Asp Tyr Ser Leu
                 85                  90                  95

Thr Ile Ala Asn Leu Gln Pro Glu Asp Ile Ala Thr Tyr Phe Cys Gln
            100                 105                 110

Gln Gly Asn Thr Leu Pro Trp Thr Phe Gly Gly Gly Thr Lys Leu Val
        115                 120                 125

Thr Lys Arg Glu Leu Gly Gly Gly Ser Gly Gly Gly Gly Ser Gly
    130                 135                 140

Gly Gly Gly Ser Ile Asp Glu Val Gln Leu Gln Ser Gly Pro Glu
145                 150                 155                 160

Leu Val Lys Pro Gly Ala Ser Met Thr Met Ser Cys Lys Ala Ser Gly
                165                 170                 175

Tyr Ser Phe Thr Gly Tyr Ile Val Asn Trp Leu Lys Gln Ser His Gly
            180                 185                 190

Lys Asn Leu Glu Trp Ile Gly Leu Ile Asn Pro Trp Lys Gly Leu Thr
        195                 200                 205

Thr Tyr Asn Gln Lys Phe Lys Gly Lys Ala Thr Leu Thr Val Asp Lys
    210                 215                 220

Ser Ser Ser Thr Ala Tyr Met Glu Leu Leu Ser Leu Thr Ser Glu Asp
225                 230                 235                 240

Ser Ala Val Tyr Tyr Cys Ala Arg Ser Gly Tyr Tyr Gly Asp Ser Asp
                245                 250                 255

Trp Tyr Phe Asp Val Trp Gly Ala Gly Thr Thr Cys Thr Val Ser Ser
            260                 265                 270

Phe Glu Ser Asp Gln Ser Asn Ser Glu Glu Ala Lys Lys Glu Glu Ala
        275                 280                 285

Lys Lys Glu Glu Ala Lys Lys Ser Asn Ser Leu Glu Ser Leu
    290                 295                 300
```

<210> SEQ ID NO 19

```
<211> LENGTH: 30
<212> TYPE: PRT
<213> ORGANISM: Homo sapiens

<400> SEQUENCE: 19

Asp Gln Glu Pro Lys Ser Cys Asp Lys Thr His Thr Cys Pro Pro Cys
 1               5                  10                  15

Pro Ala Pro Glu Leu Leu Gly Gly Pro Ser Val Phe Leu Phe
            20                  25                  30

<210> SEQ ID NO 20
<211> LENGTH: 30
<212> TYPE: PRT
<213> ORGANISM: Homo sapiens

<400> SEQUENCE: 20

Asp Gln Glu Pro Lys Ser Ser Asp Lys Thr His Thr Ser Pro Pro Ser
 1               5                  10                  15

Pro Ala Pro Glu Leu Leu Gly Gly Ser Ser Val Phe Leu Phe
            20                  25                  30

<210> SEQ ID NO 21
<211> LENGTH: 30
<212> TYPE: PRT
<213> ORGANISM: Homo sapiens

<400> SEQUENCE: 21

Asp Gln Glu Pro Lys Ser Ser Asp Lys Thr His Thr Ser Pro Pro Ser
 1               5                  10                  15

Pro Ala Pro Glu Leu Leu Gly Gly Pro Ser Val Phe Leu Phe
            20                  25                  30

<210> SEQ ID NO 22
<211> LENGTH: 30
<212> TYPE: PRT
<213> ORGANISM: Homo sapiens

<400> SEQUENCE: 22

Asp Gln Glu Pro Lys Ser Ser Asp Lys Thr His Thr Ser Pro Pro Ser
 1               5                  10                  15

Pro Ala Pro Glu Phe Glu Gly Ala Pro Ser Val Phe Leu Phe
            20                  25                  30

<210> SEQ ID NO 23
<211> LENGTH: 30
<212> TYPE: PRT
<213> ORGANISM: Homo sapiens

<400> SEQUENCE: 23

Asp Gln Glu Pro Lys Ser Cys Asp Lys Thr His Thr Cys Pro Pro Cys
 1               5                  10                  15

Pro Ala Pro Glu Phe Glu Gly Ala Pro Ser Val Phe Leu Phe
            20                  25                  30

<210> SEQ ID NO 24
<211> LENGTH: 30
<212> TYPE: PRT
<213> ORGANISM: Homo sapiens

<400> SEQUENCE: 24

Asp Gln Glu Pro Lys Ser Cys Asp Lys Thr His Thr Cys Pro Pro Cys
 1               5                  10                  15
```

Pro Ala Pro Glu Leu Leu Gly Gly Pro Ser Val Phe Leu Pro
            20                  25                  30

<210> SEQ ID NO 25
<211> LENGTH: 30
<212> TYPE: PRT
<213> ORGANISM: Homo sapiens

<400> SEQUENCE: 25

Asp Gln Glu Pro Lys Ser Cys Asp Lys Thr His Thr Cys Pro Pro Cys
1               5                   10                  15

Pro Ala Pro Glu Phe Glu Gly Ala Pro Ser Val Phe Leu Pro
            20                  25                  30

<210> SEQ ID NO 26
<211> LENGTH: 30
<212> TYPE: PRT
<213> ORGANISM: Homo sapiens

<400> SEQUENCE: 26

Asp Gln Glu Pro Lys Ser Ser Asp Lys Thr His Thr Ser Pro Pro Ser
1               5                   10                  15

Pro Ala Pro Glu Leu Leu Gly Gly Pro Ser Val Phe Leu Pro
            20                  25                  30

<210> SEQ ID NO 27
<211> LENGTH: 30
<212> TYPE: PRT
<213> ORGANISM: Homo sapiens

<400> SEQUENCE: 27

Asp Gln Glu Pro Lys Ser Ser Asp Lys Thr His Thr Ser Pro Pro Ser
1               5                   10                  15

Pro Ala Pro Glu Leu Leu Gly Gly Ser Ser Val Phe Leu Pro
            20                  25                  30

<210> SEQ ID NO 28
<211> LENGTH: 30
<212> TYPE: PRT
<213> ORGANISM: Homo sapiens

<400> SEQUENCE: 28

Asp Gln Glu Pro Lys Ser Ser Asp Lys Thr His Thr Ser Pro Pro Ser
1               5                   10                  15

Pro Ala Pro Glu Phe Glu Gly Ala Pro Ser Val Phe Leu Pro
            20                  25                  30

<210> SEQ ID NO 29
<211> LENGTH: 916
<212> TYPE: DNA
<213> ORGANISM: Homo sapiens
<220> FEATURE:
<221> NAME/KEY: CDS
<222> LOCATION: (7)..(915)

<400> SEQUENCE: 29 aagctt atg gat ttt caa gtg cag att ttc agc ttc ctg cta atc agt      48
       Met Asp Phe Gln Val Gln Ile Phe Ser Phe Leu Leu Ile Ser
       1               5                   10 gct tca gtc ata atg tcc aga gga gtc gac atc cag atg aca cag act    96
Ala Ser Val Ile Met Ser Arg Gly Val Asp Ile Gln Met Thr Gln Thr
15                  20                  25                  30 aca tcc tcc ctg tct gcc tct ctg gga gac aga gtc acc atc agt tgc    144

| | | | | | | | | | | | | | | | |
|---|---|---|---|---|---|---|---|---|---|---|---|---|---|---|---|
|Thr|Ser|Ser|Leu|Ser|Ala|Ser|Leu|Gly|Asp|Arg|Val|Thr|Ile|Ser|Cys|
| | | | |35| | | | |40| | | | |45| |

```
agg gca agt cag gac att cgc aat tat tta aac tgg tat cag cag aaa      192
Arg Ala Ser Gln Asp Ile Arg Asn Tyr Leu Asn Trp Tyr Gln Gln Lys
             50                  55                  60 cca gat gga act gtt aaa ctc ctg atc tac tac aca tca aga tta cac      240
Pro Asp Gly Thr Val Lys Leu Leu Ile Tyr Tyr Thr Ser Arg Leu His
         65                  70                  75 tca gga gtc cca tca agg ttc agt ggc agt ggg tct gga aca gat tat      288
Ser Gly Val Pro Ser Arg Phe Ser Gly Ser Gly Ser Gly Thr Asp Tyr
 80                  85                  90 tct ctc acc att gcc aac ctg caa cca gaa gat att gcc act tac ttt      336
Ser Leu Thr Ile Ala Asn Leu Gln Pro Glu Asp Ile Ala Thr Tyr Phe
 95                 100                 105                 110 tgc caa cag ggt aat acg ctt ccg tgg acg ttc ggt gga ggc acc aaa      384
Cys Gln Gln Gly Asn Thr Leu Pro Trp Thr Phe Gly Gly Gly Thr Lys
                115                 120                 125 ctg gta acc aaa cgg gag ctc ggt ggc ggt ggc tcg ggc ggt ggt ggg      432
Leu Val Thr Lys Arg Glu Leu Gly Gly Gly Gly Ser Gly Gly Gly Gly
            130                 135                 140 tcg ggt ggc ggc gga tct atc gat gag gtc cag ctg caa cag tct gga      480
Ser Gly Gly Gly Gly Ser Ile Asp Glu Val Gln Leu Gln Gln Ser Gly
        145                 150                 155 cct gaa ctg gtg aag cct gga gct tca atg aca atg tcc tgc aag gcc      528
Pro Glu Leu Val Lys Pro Gly Ala Ser Met Thr Met Ser Cys Lys Ala
    160                 165                 170 tct ggt tac tca ttc act ggc tac atc gtg aac tgg ctg aag cag agc      576
Ser Gly Tyr Ser Phe Thr Gly Tyr Ile Val Asn Trp Leu Lys Gln Ser
175                 180                 185                 190 cat gga aag aac ctt gag tgg att gga ctt att aat cca tac aaa ggt      624
His Gly Lys Asn Leu Glu Trp Ile Gly Leu Ile Asn Pro Tyr Lys Gly
                195                 200                 205 ctt act acc tac aac cag aaa ttc aag ggc aag gcc aca tta act gta      672
Leu Thr Thr Tyr Asn Gln Lys Phe Lys Gly Lys Ala Thr Leu Thr Val
            210                 215                 220 gac aag tca tcc agc aca gcc tac atg gag ctc ctc agt ctg aca tct      720
Asp Lys Ser Ser Ser Thr Ala Tyr Met Glu Leu Leu Ser Leu Thr Ser
        225                 230                 235 gaa gac tct gca gtc tat tac tgt gca aga tct ggg tac tat ggt gac      768
Glu Asp Ser Ala Val Tyr Tyr Cys Ala Arg Ser Gly Tyr Tyr Gly Asp
    240                 245                 250 tcg gac tgg tac ttc gat gtc tgg ggc gca ggg acc acg tgc acc gtc      816
Ser Asp Trp Tyr Phe Asp Val Trp Gly Ala Gly Thr Thr Cys Thr Val
255                 260                 265                 270 tcc tca ttc gaa taa tct gat caa tcc aac tct gaa gaa gca aag aaa      864
Ser Ser Phe Glu     Ser Asp Gln Ser Asn Ser Glu Glu Ala Lys Lys
                275                 280                 285 gag gag gcc aaa aag gag gaa gcc aag aaa tct aac agc ctc gag agc      912
Glu Glu Ala Lys Lys Glu Glu Ala Lys Lys Ser Asn Ser Leu Glu Ser
            290                 295                 300 cta g                                                                916
Leu
```

<210> SEQ ID NO 30
<211> LENGTH: 274
<212> TYPE: PRT
<213> ORGANISM: Homo sapiens

<400> SEQUENCE: 30

Met Asp Phe Gln Val Gln Ile Phe Ser Phe Leu Leu Ile Ser Ala Ser

```
                 1               5                  10                 15
Val Ile Met Ser Arg Gly Val Asp Ile Gln Met Thr Gln Thr Thr Ser
                20                 25                 30
Ser Leu Ser Ala Ser Leu Gly Asp Arg Val Thr Ile Ser Cys Arg Ala
                35                 40                 45
Ser Gln Asp Ile Arg Asn Tyr Leu Asn Trp Tyr Gln Gln Lys Pro Asp
                50                 55                 60
Gly Thr Val Lys Leu Leu Ile Tyr Tyr Thr Ser Arg Leu His Ser Gly
 65                 70                 75                 80
Val Pro Ser Arg Phe Ser Gly Ser Gly Ser Gly Thr Asp Tyr Ser Leu
                 85                 90                 95
Thr Ile Ala Asn Leu Gln Pro Glu Asp Ile Ala Thr Tyr Phe Cys Gln
                100                105                110
Gln Gly Asn Thr Leu Pro Trp Thr Phe Gly Gly Gly Thr Lys Leu Val
                115                120                125
Thr Lys Arg Glu Leu Gly Gly Gly Ser Gly Gly Gly Gly Ser Gly
                130                135                140
Gly Gly Gly Ser Ile Asp Glu Val Gln Leu Gln Gln Ser Gly Pro Glu
145                150                155                160
Leu Val Lys Pro Gly Ala Ser Met Thr Met Ser Cys Lys Ala Ser Gly
                165                170                175
Tyr Ser Phe Thr Gly Tyr Ile Val Asn Trp Leu Lys Gln Ser His Gly
                180                185                190
Lys Asn Leu Glu Trp Ile Gly Leu Ile Asn Pro Tyr Lys Gly Leu Thr
                195                200                205
Thr Tyr Asn Gln Lys Phe Lys Gly Lys Ala Thr Leu Thr Val Asp Lys
                210                215                220
Ser Ser Ser Thr Ala Tyr Met Glu Leu Leu Ser Leu Thr Ser Glu Asp
225                230                235                240
Ser Ala Val Tyr Tyr Cys Ala Arg Ser Gly Tyr Tyr Gly Asp Ser Asp
                245                250                255
Trp Tyr Phe Asp Val Trp Gly Ala Gly Thr Thr Cys Thr Val Ser Ser
                260                265                270
Phe Glu

<210> SEQ ID NO 31
<211> LENGTH: 28
<212> TYPE: PRT
<213> ORGANISM: Homo sapiens

<400> SEQUENCE: 31

Ser Asp Gln Ser Asn Ser Glu Glu Ala Lys Lys Glu Glu Ala Lys Lys
 1               5                  10                 15
Glu Glu Ala Lys Lys Ser Asn Ser Leu Glu Ser Leu
                20                 25

<210> SEQ ID NO 32
<211> LENGTH: 302
<212> TYPE: PRT
<213> ORGANISM: Homo sapiens

<400> SEQUENCE: 32

Met Asp Phe Gln Val Gln Ile Phe Ser Phe Leu Leu Ile Ser Ala Ser
 1               5                  10                 15
Val Ile Met Ser Arg Gly Val Asp Ile Gln Met Thr Gln Thr Thr Ser
                20                 25                 30
```

-continued

```
Ser Leu Ser Ala Ser Leu Gly Asp Arg Val Thr Ile Ser Cys Arg Ala
        35                  40                  45

Ser Gln Asp Ile Arg Asn Tyr Leu Asn Trp Tyr Gln Gln Lys Pro Asp
    50                  55                  60

Gly Thr Val Lys Leu Leu Ile Tyr Tyr Thr Ser Arg Leu His Ser Gly
65                  70                  75                  80

Val Pro Ser Arg Phe Ser Gly Ser Gly Ser Gly Thr Asp Tyr Ser Leu
                85                  90                  95

Thr Ile Ala Asn Leu Gln Pro Glu Asp Ile Ala Thr Tyr Phe Cys Gln
            100                 105                 110

Gln Gly Asn Thr Leu Pro Trp Thr Phe Gly Gly Gly Thr Lys Leu Val
        115                 120                 125

Thr Lys Arg Glu Leu Gly Gly Gly Gly Ser Gly Gly Gly Gly Ser Gly
    130                 135                 140

Gly Gly Gly Ser Ile Asp Glu Val Gln Leu Gln Gln Ser Gly Pro Glu
145                 150                 155                 160

Leu Val Lys Pro Gly Ala Ser Met Thr Met Ser Cys Lys Ala Ser Gly
                165                 170                 175

Tyr Ser Phe Thr Gly Tyr Ile Val Asn Trp Leu Lys Gln Ser His Gly
            180                 185                 190

Lys Asn Leu Glu Trp Ile Gly Leu Ile Asn Pro Tyr Lys Gly Leu Thr
        195                 200                 205

Thr Tyr Asn Gln Lys Phe Lys Gly Lys Ala Thr Leu Thr Val Asp Lys
    210                 215                 220

Ser Ser Ser Thr Ala Tyr Met Glu Leu Leu Ser Leu Thr Ser Glu Asp
225                 230                 235                 240

Ser Ala Val Tyr Tyr Cys Ala Arg Ser Gly Tyr Tyr Gly Asp Ser Asp
                245                 250                 255

Trp Tyr Phe Asp Val Trp Gly Ala Gly Thr Thr Cys Thr Val Ser Ser
            260                 265                 270

Phe Glu Ser Asp Gln Ser Asn Ser Glu Glu Ala Lys Lys Glu Glu Ala
        275                 280                 285

Lys Lys Glu Glu Ala Lys Lys Ser Asn Ser Leu Glu Ser Leu
    290                 295                 300
```